US008489176B1

(12) United States Patent
Ben-David et al.

(10) Patent No.: US 8,489,176 B1
(45) Date of Patent: Jul. 16, 2013

(54) RADIOACTIVE EMISSION DETECTOR EQUIPPED WITH A POSITION TRACKING SYSTEM AND UTILIZATION THEREOF WITH MEDICAL SYSTEMS AND IN MEDICAL PROCEDURES

(75) Inventors: Gal Ben-David, Mitzpe Adi (IL); Yoel Zilberstien, Haifa (IL); Yoav Kimchy, Haifa (IL)

(73) Assignee: Spectrum Dynamics LLC, Orangeburg, NY (US)

( * ) Notice: Subject to any disclaimer, the term of this patent is extended or adjusted under 35 U.S.C. 154(b) by 1417 days.

(21) Appl. No.: 09/641,973

(22) Filed: Aug. 21, 2000

(51) Int. Cl.
*A61F 2/04* (2006.01)

(52) U.S. Cl.
USPC ............... 600/436; 600/3; 600/407; 606/130; 702/152

(58) Field of Classification Search
USPC ................. 600/407, 410, 411, 413, 414, 415, 600/417, 420, 431, 425–429, 436, 424, 3; 606/130, 120; 702/152; 378/21
See application file for complete search history.

(56) References Cited

U.S. PATENT DOCUMENTS

| 630,611 | A | 8/1899 | Knapp et al. |
|---|---|---|---|
| 2,776,377 | A | 1/1957 | Anger |
| 3,340,866 | A | 9/1967 | Nöller |
| 3,446,965 | A | 5/1969 | Ogier et al. |
| 3,535,085 | A | 10/1970 | Shumate et al. |
| 3,684,887 | A | 8/1972 | Hugonin |
| 3,690,309 | A | 9/1972 | Pluzhnikov et al. |
| 3,719,183 | A | 3/1973 | Schwartz |
| 3,739,279 | A | 6/1973 | Hollis |
| 3,971,362 | A | 7/1976 | Pope et al. |
| 3,978,337 | A | 8/1976 | Nickles et al. |
| 3,988,585 | A | 10/1976 | O'Neill et al. |
| 4,000,502 | A | 12/1976 | Butler et al. |
| 4,015,592 | A | 4/1977 | Bradley-Moore |
| 4,055,765 | A | 10/1977 | Gerber et al. |
| 4,061,919 | A | 12/1977 | Miller et al. |
| 4,095,107 | A | 6/1978 | Genna et al. |
| 4,165,462 | A | 8/1979 | Macovski et al. |
| 4,181,856 | A | 1/1980 | Bone |

(Continued)

FOREIGN PATENT DOCUMENTS

| DE | 1516429 | 12/1969 |
|---|---|---|
| DE | 19814199 | 7/1999 |

(Continued)

OTHER PUBLICATIONS

Computer Assisted Collimation Gamma Camera: A New Approach to Imaging Contaminated Tissues. M. Quartuccio; D. Franck; P. Pihet; S. Begot; C. Jeanguillaume. Radiation Protection Dosimetry. vol. 89, Nos. 3-4, pp. 343-348, (2000). Nuclear Technology Publishing.

(Continued)

*Primary Examiner* — Unsu Jung
*Assistant Examiner* — Joseph M Santos

(57) ABSTRACT

A system for calculating a position of a radioactivity emitting source in a system-of-coordinates, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for calculating the position of the radioactivity emitting source in the system-of-coordinates.

27 Claims, 4 Drawing Sheets

U.S. PATENT DOCUMENTS

| | | | |
|---|---|---|---|
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A | 12/1988 | Brunnett |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledly |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,863 A | 8/1991 | Matsuno et al. |
| 5,042,056 A | 8/1991 | Hellmick et al. |
| 5,070,878 A | 12/1991 | Denen |
| 5,088,492 A | 2/1992 | Takayama et al. |
| 5,115,137 A | 5/1992 | Andersson-Engels et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A * | 3/1994 | Wessels ............... 378/163 |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A | 1/1995 | Drane |
| 5,381,791 A | 1/1995 | Qian |
| 5,383,456 A | 1/1995 | Arnold et al. |
| 5,383,858 A | 1/1995 | Reilly et al. |
| 5,386,446 A * | 1/1995 | Fujimoto et al. ............ 378/20 |
| 5,387,409 A | 2/1995 | Nunn et al. |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hofgrefe et al. |
| 5,431,161 A | 7/1995 | Ryals et al. |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misik et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A * | 12/1997 | Taylor et al. ............... 606/130 |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |

| | | | | | | |
|---|---|---|---|---|---|---|
| 5,779,675 A | 7/1998 | Reilly et al. | | 6,072,177 A | 6/2000 | McCroskey et al. |
| 5,780,855 A | 7/1998 | Pare et al. | | 6,076,009 A | 6/2000 | Raylman et al. |
| 5,781,442 A | 7/1998 | Engleson et al. | | 6,080,984 A | 6/2000 | Friesenhahn |
| 5,784,432 A | 7/1998 | Kurtz et al. | | D428,491 S | 7/2000 | Beale et al. |
| 5,786,597 A | 7/1998 | Lingren et al. | | 6,082,366 A | 7/2000 | Andra et al. |
| 5,795,333 A | 8/1998 | Reilly et al. | | 6,090,064 A | 7/2000 | Reilly et al. |
| 5,800,355 A | 9/1998 | Hasegawa | | 6,091,070 A | 7/2000 | Lingren et al. |
| 5,806,519 A | 9/1998 | Evans, III et al. | | 6,096,011 A | 8/2000 | Trombley, III et al. |
| 5,808,203 A | 9/1998 | Nolan, Jr. et al. | | 6,107,102 A | 8/2000 | Ferrari |
| 5,810,742 A | 9/1998 | Pearlman | | 6,115,635 A | 9/2000 | Bourgeois |
| 5,811,814 A | 9/1998 | Leone et al. | | 6,129,670 A | 10/2000 | Burdette et al. |
| 5,813,985 A | 9/1998 | Carroll | | 6,132,372 A | 10/2000 | Essen-Moller |
| 5,818,050 A | 10/1998 | Dilmanian et al. | | 6,135,955 A | 10/2000 | Madden et al. |
| 5,821,541 A | 10/1998 | Tümer | | 6,135,968 A | 10/2000 | Brounstein |
| 5,825,031 A | 10/1998 | Wong et al. | | 6,137,109 A | 10/2000 | Hayes |
| 5,827,219 A | 10/1998 | Uber, III et al. | | 6,145,277 A | 11/2000 | Lawecki et al. |
| 5,828,073 A | 10/1998 | Zhu et al. | | 6,147,352 A | 11/2000 | Ashburn |
| 5,833,603 A | 11/1998 | Kovacs et al. | | 6,147,353 A | 11/2000 | Gagnon et al. |
| 5,838,009 A | 11/1998 | Plummer et al. | | 6,148,229 A | 11/2000 | Morris, Sr. et al. |
| 5,840,026 A | 11/1998 | Uber, III et al. | | 6,149,627 A | 11/2000 | Uber, III |
| 5,841,141 A | 11/1998 | Gullberg et al. | | 6,155,485 A | 12/2000 | Coughlin et al. |
| 5,842,977 A | 12/1998 | Lesho et al. | | 6,160,398 A | 12/2000 | Walsh |
| 5,843,037 A | 12/1998 | Uber, III | | 6,162,198 A | 12/2000 | Coffey et al. |
| 5,846,513 A | 12/1998 | Carroll et al. | | 6,172,362 B1 | 1/2001 | Lingren et al. |
| 5,847,396 A | 12/1998 | Lingren et al. | | 6,173,201 B1 * | 1/2001 | Front ........................... 600/429 |
| 5,857,463 A * | 1/1999 | Thurston et al. ............... 600/436 | | 6,184,530 B1 | 2/2001 | Hines et al. |
| 5,871,013 A * | 2/1999 | Wainer et al. ................. 600/407 | | 6,189,195 B1 | 2/2001 | Reilly et al. |
| 5,873,861 A | 2/1999 | Hitchins et al. | | 6,194,715 B1 | 2/2001 | Lingren et al. |
| 5,880,475 A | 3/1999 | Oka et al. | | 6,194,725 B1 | 2/2001 | Colsher et al. |
| 5,882,338 A | 3/1999 | Gray | | 6,194,726 B1 | 2/2001 | Pi et al. |
| 5,884,457 A | 3/1999 | Ortiz et al. | | 6,197,000 B1 | 3/2001 | Reilly et al. |
| 5,885,216 A | 3/1999 | Evans, III et al. | | 6,202,923 B1 | 3/2001 | Boyer et al. |
| 5,891,030 A | 4/1999 | Johnson et al. | | 6,203,775 B1 | 3/2001 | Torchilin et al. |
| 5,893,397 A | 4/1999 | Peterson et al. | | 6,205,347 B1 | 3/2001 | Morgan et al. |
| 5,899,885 A | 5/1999 | Reilly et al. | | 6,212,423 B1 | 4/2001 | Krakovitz |
| 5,900,533 A | 5/1999 | Chou | | 6,223,065 B1 | 4/2001 | Misic et al. |
| 5,903,008 A | 5/1999 | Li | | 6,224,577 B1 | 5/2001 | Dedola et al. |
| 5,910,112 A | 6/1999 | Judd et al. | | 6,226,350 B1 | 5/2001 | Hsieh |
| 5,911,252 A | 6/1999 | Cassel | | 6,229,145 B1 | 5/2001 | Weinberg |
| 5,916,167 A | 6/1999 | Kramer et al. | | 6,232,605 B1 | 5/2001 | Soluri et al. |
| 5,916,197 A | 6/1999 | Reilly et al. | | 6,233,304 B1 | 5/2001 | Hu et al. |
| 5,920,054 A | 7/1999 | Uber, III | | 6,236,050 B1 | 5/2001 | Tumer |
| 5,927,351 A | 7/1999 | Zhu et al. | | 6,236,878 B1 | 5/2001 | Taylor et al. |
| 5,928,150 A | 7/1999 | Call | | 6,236,880 B1 | 5/2001 | Raylman et al. |
| 5,932,879 A | 8/1999 | Raylman et al. | | 6,239,438 B1 * | 5/2001 | Schubert .................. 250/363.03 |
| 5,938,639 A | 8/1999 | Reilly et al. | | 6,240,312 B1 | 5/2001 | Alfano et al. |
| 5,939,724 A | 8/1999 | Eisen et al. | | 6,241,708 B1 | 6/2001 | Reilly et al. |
| 5,944,190 A | 8/1999 | Edelen | | 6,242,743 B1 | 6/2001 | DeVito et al. |
| 5,944,694 A | 8/1999 | Hitchins et al. | | 6,242,744 B1 | 6/2001 | Soluri et al. |
| 5,947,935 A | 9/1999 | Rhinehart et al. | | 6,242,745 B1 | 6/2001 | Berlad et al. |
| 5,953,884 A | 9/1999 | Lawecki et al. | | 6,246,901 B1 | 6/2001 | Benaron |
| 5,954,668 A | 9/1999 | Uber, III et al. | | 6,252,924 B1 | 6/2001 | Davantes et al. |
| 5,961,457 A | 10/1999 | Raylman et al. | | 6,258,576 B1 | 7/2001 | Richards-Kortum et al. |
| 5,967,983 A | 10/1999 | Ashburn | | 6,259,095 B1 | 7/2001 | Bouton et al. |
| 5,973,598 A | 10/1999 | Beigel | | 6,261,562 B1 | 7/2001 | Xu et al. |
| 5,974,165 A | 10/1999 | Giger et al. | | 6,263,229 B1 | 7/2001 | Atalar et al. |
| 5,984,860 A | 11/1999 | Shan | | 6,269,340 B1 | 7/2001 | Ford et al. |
| 5,987,350 A | 11/1999 | Thurston | | 6,270,463 B1 | 8/2001 | Morris, Sr. et al. |
| 5,993,378 A | 11/1999 | Lemelson | | 6,271,524 B1 | 8/2001 | Wainer et al. |
| 5,997,502 A | 12/1999 | Reilly et al. | | 6,271,525 B1 | 8/2001 | Majewski et al. |
| 6,002,134 A | 12/1999 | Lingren | | 6,280,704 B1 | 8/2001 | Schutt et al. |
| 6,002,480 A | 12/1999 | Izatt et al. | | 6,281,505 B1 | 8/2001 | Hines et al. |
| 6,017,330 A | 1/2000 | Hitchins et al. | | 6,308,097 B1 | 10/2001 | Pearlman |
| 6,019,745 A | 2/2000 | Gray | | 6,310,968 B1 | 10/2001 | Hawkins et al. |
| 6,021,341 A | 2/2000 | Scibilia et al. | | 6,315,981 B1 | 11/2001 | Unger |
| 6,026,317 A | 2/2000 | Verani | | 6,317,623 B1 | 11/2001 | Griffiths et al. |
| 6,037,595 A | 3/2000 | Lingren | | 6,317,648 B1 | 11/2001 | Sleep et al. |
| 6,040,697 A | 3/2000 | Misic | | 6,318,630 B1 | 11/2001 | Coughlin et al. |
| 6,042,565 A | 3/2000 | Hirschman et al. | | 6,322,535 B1 | 11/2001 | Hitchins et al. |
| RE36,648 E | 4/2000 | Uber, III et al. | | 6,323,648 B1 | 11/2001 | Belt et al. |
| 6,046,454 A | 4/2000 | Lingren et al. | | 6,324,418 B1 | 11/2001 | Crowley et al. |
| 6,048,334 A | 4/2000 | Hirschman et al. | | RE37,487 E | 12/2001 | Reilly et al. |
| 6,052,618 A | 4/2000 | Dahlke et al. | | D452,737 S | 1/2002 | Nolan, Jr. et al. |
| 6,055,450 A | 4/2000 | Ashburn | | 6,336,913 B1 | 1/2002 | Spohn et al. |
| 6,055,452 A | 4/2000 | Pearlman | | 6,339,652 B1 | 1/2002 | Hawkins et al. |
| RE36,693 E | 5/2000 | Reich | | 6,339,718 B1 | 1/2002 | Zatezalo et al. |
| 6,063,052 A | 5/2000 | Uber et al. | | 6,344,745 B1 | 2/2002 | Reisker et al. |
| D426,891 S | 6/2000 | Beale et al. | | 6,346,706 B1 | 2/2002 | Rogers et al. |
| D426,892 S | 6/2000 | Beale et al. | | 6,346,886 B1 | 2/2002 | de la Huerga |

| Patent No. | Kind | Date | Inventors | Class |
|---|---|---|---|---|
| RE37,602 | E | 3/2002 | Uber, III et al. | |
| 6,353,227 | B1 | 3/2002 | Boxen | |
| 6,356,081 | B1 | 3/2002 | Misic | |
| 6,368,331 | B1* | 4/2002 | Front et al. | 606/130 |
| 6,371,938 | B1 | 4/2002 | Reilly et al. | |
| 6,375,624 | B1 | 4/2002 | Uber, III et al. | |
| 6,377,838 | B1 | 4/2002 | Iwanczyk et al. | |
| 6,381,349 | B1 | 4/2002 | Zeng et al. | |
| 6,385,483 | B1 | 5/2002 | Uber, III et al. | |
| 6,388,258 | B1 | 5/2002 | Berlad et al. | |
| 6,392,235 | B1 | 5/2002 | Barrett et al. | |
| 6,396,273 | B2 | 5/2002 | Misic | |
| 6,397,098 | B1 | 5/2002 | Uber, III et al. | |
| 6,399,951 | B1 | 6/2002 | Paulus et al. | |
| 6,402,717 | B1 | 6/2002 | Reilly et al. | |
| 6,402,718 | B1 | 6/2002 | Reilly et al. | |
| 6,407,391 | B1 | 6/2002 | Mastrippolito et al. | |
| 6,408,204 | B1 | 6/2002 | Hirschman | |
| 6,409,987 | B1 | 6/2002 | Cardin et al. | |
| 6,415,046 | B1 | 7/2002 | Kerut, Sr. | |
| 6,420,711 | B2 | 7/2002 | Tuemer | |
| 6,425,174 | B1 | 7/2002 | Riech | |
| 6,426,917 | B1 | 7/2002 | Tabanou et al. | |
| 6,429,431 | B1 | 8/2002 | Wilk | |
| 6,431,175 | B1 | 8/2002 | Penner et al. | |
| 6,432,089 | B1 | 8/2002 | Kakimi et al. | |
| 6,438,401 | B1 | 8/2002 | Cheng et al. | |
| 6,439,444 | B1 | 8/2002 | Shields, II | |
| 6,440,107 | B1 | 8/2002 | Trombley, III et al. | |
| 6,442,418 | B1 | 8/2002 | Evans, III et al. | |
| 6,448,560 | B1 | 9/2002 | Tumer | |
| 6,453,199 | B1 | 9/2002 | Kobozev | |
| 6,459,925 | B1 | 10/2002 | Nields et al. | |
| 6,459,931 | B1 | 10/2002 | Hirschman | |
| 6,468,261 | B1 | 10/2002 | Small et al. | |
| 6,469,306 | B1 | 10/2002 | Van Dulmen et al. | |
| 6,471,674 | B1 | 10/2002 | Emig et al. | |
| 6,480,732 | B1 | 11/2002 | Tanaka et al. | |
| 6,484,051 | B1 | 11/2002 | Daniel | |
| 6,488,661 | B1 | 12/2002 | Spohn et al. | |
| 6,490,476 | B1 | 12/2002 | Townsend et al. | |
| 6,504,157 | B2 | 1/2003 | Juhi | |
| 6,504,178 | B2 | 1/2003 | Carlson et al. | |
| 6,504,899 | B2 | 1/2003 | Pugachev et al. | |
| 6,506,155 | B2 | 1/2003 | Sluis et al. | |
| 6,510,336 | B1 | 1/2003 | Daghighian et al. | |
| 6,512,374 | B1 | 1/2003 | Misic et al. | |
| 6,516,213 | B1 | 2/2003 | Nevo | |
| 6,519,569 | B1 | 2/2003 | White et al. | |
| 6,520,930 | B2 | 2/2003 | Critchlow et al. | |
| 6,522,945 | B2 | 2/2003 | Sleep et al. | |
| 6,525,320 | B1 | 2/2003 | Juni | |
| 6,525,321 | B1 | 2/2003 | Juni | |
| 6,541,763 | B2 | 4/2003 | Lingren et al. | |
| 6,545,280 | B2 | 4/2003 | Weinberg et al. | |
| 6,549,646 | B1 | 4/2003 | Yeh et al. | |
| 6,560,354 | B1* | 5/2003 | Maurer et al. | 382/131 |
| 6,562,008 | B1 | 5/2003 | Reilly et al. | |
| 6,563,942 | B2 | 5/2003 | Takeo et al. | |
| 6,565,502 | B1 | 5/2003 | Bede et al. | |
| 6,567,687 | B2 | 5/2003 | Front et al. | |
| 6,575,930 | B1 | 6/2003 | Trombley, III et al. | |
| 6,576,918 | B1 | 6/2003 | Fu et al. | |
| 6,584,348 | B2 | 6/2003 | Glukhovsky | |
| 6,585,700 | B1 | 7/2003 | Trocki et al. | |
| 6,587,710 | B1 | 7/2003 | Wainer | |
| 6,589,158 | B2 | 7/2003 | Winkler | |
| 6,591,127 | B1 | 7/2003 | McKinnon | |
| 6,592,520 | B1 | 7/2003 | Peszynski et al. | |
| 6,602,488 | B1 | 8/2003 | Daghighian | |
| 6,607,301 | B1 | 8/2003 | Glukhovsky et al. | |
| 6,611,141 | B1 | 8/2003 | Schulz et al. | |
| 6,614,453 | B1 | 9/2003 | Suri et al. | |
| 6,620,134 | B1 | 9/2003 | Trombley, III et al. | |
| 6,627,893 | B1 | 9/2003 | Zeng et al. | |
| 6,628,983 | B1 | 9/2003 | Gagnon | |
| 6,628,984 | B2 | 9/2003 | Weinberg | |
| 6,630,735 | B1 | 10/2003 | Carlson et al. | |
| 6,631,284 | B2 | 10/2003 | Nutt et al. | |
| 6,632,216 | B2 | 10/2003 | Houzego et al. | |
| 6,633,658 | B1 | 10/2003 | Dabney et al. | |
| 6,638,752 | B2 | 10/2003 | Contag et al. | |
| 6,643,537 | B1 | 11/2003 | Zatezalo et al. | |
| 6,643,538 | B1 | 11/2003 | Majewski et al. | |
| 6,652,489 | B2 | 11/2003 | Trocki et al. | |
| 6,657,200 | B2 | 12/2003 | Nygard et al. | |
| 6,662,036 | B2* | 12/2003 | Cosman | 600/411 |
| 6,664,542 | B2 | 12/2003 | Ye et al. | |
| 6,670,258 | B2 | 12/2003 | Carlson et al. | |
| 6,671,563 | B1 | 12/2003 | Engleson et al. | |
| 6,673,033 | B1 | 1/2004 | Sciulli et al. | |
| 6,674,834 | B1 | 1/2004 | Acharya et al. | |
| 6,676,634 | B1 | 1/2004 | Spohn et al. | |
| 6,677,182 | B2 | 1/2004 | Carlson et al. | |
| 6,677,755 | B2 | 1/2004 | Belt et al. | |
| 6,680,750 | B1 | 1/2004 | Tournier et al. | |
| 6,694,172 | B1 | 2/2004 | Gagnon et al. | |
| 6,697,660 | B1 | 2/2004 | Robinson | |
| 6,699,219 | B2 | 3/2004 | Emig et al. | |
| 6,704,592 | B1 | 3/2004 | Reynolds et al. | |
| 6,713,766 | B2 | 3/2004 | Garrard et al. | |
| 6,714,012 | B2 | 3/2004 | Belt et al. | |
| 6,714,013 | B2 | 3/2004 | Misic | |
| 6,716,195 | B2 | 4/2004 | Nolan, Jr. et al. | |
| 6,722,499 | B2 | 4/2004 | Reich | |
| 6,723,988 | B1 | 4/2004 | Wainer | |
| 6,726,657 | B1 | 4/2004 | Dedig et al. | |
| 6,728,583 | B2 | 4/2004 | Hallett | |
| 6,731,971 | B2 | 5/2004 | Evans, III et al. | |
| 6,731,989 | B2 | 5/2004 | Engleson et al. | |
| 6,733,477 | B2 | 5/2004 | Cowan et al. | |
| 6,733,478 | B2 | 5/2004 | Reilly et al. | |
| 6,734,416 | B2 | 5/2004 | Carlson et al. | |
| 6,734,430 | B2 | 5/2004 | Soluri et al. | |
| 6,737,652 | B2 | 5/2004 | Lanza et al. | |
| 6,737,866 | B2 | 5/2004 | Belt et al. | |
| 6,740,882 | B2 | 5/2004 | Weinberg et al. | |
| 6,743,202 | B2 | 6/2004 | Hirschman et al. | |
| 6,743,205 | B2 | 6/2004 | Nolan, Jr. et al. | |
| 6,747,454 | B2 | 6/2004 | Belt | |
| 6,748,259 | B1 | 6/2004 | Benaron et al. | |
| 6,751,500 | B2 | 6/2004 | Hirschman et al. | |
| 6,765,981 | B2 | 7/2004 | Heumann | |
| 6,766,048 | B1 | 7/2004 | Launay et al. | |
| 6,771,802 | B1* | 8/2004 | Patt et al. | 382/128 |
| 6,774,358 | B2 | 8/2004 | Hamill et al. | |
| 6,776,977 | B2 | 8/2004 | Liu | |
| 6,787,777 | B1 | 9/2004 | Gagnon et al. | |
| 6,788,758 | B2 | 9/2004 | De Villiers | |
| 6,798,206 | B2 | 9/2004 | Misic | |
| 6,808,513 | B2 | 10/2004 | Reilly et al. | |
| 6,813,868 | B2 | 11/2004 | Baldwin et al. | |
| 6,821,013 | B2 | 11/2004 | Reilly et al. | |
| 6,822,237 | B2 | 11/2004 | Inoue et al. | |
| 6,833,705 | B2 | 12/2004 | Misic | |
| 6,838,672 | B2 | 1/2005 | Wagenaar et al. | |
| 6,841,782 | B1 | 1/2005 | Balan et al. | |
| 6,843,357 | B2 | 1/2005 | Bybee et al. | |
| 6,851,615 | B2 | 2/2005 | Jones | |
| 6,866,654 | B2 | 3/2005 | Callan et al. | |
| 6,870,175 | B2 | 3/2005 | Dell et al. | |
| 6,881,043 | B2 | 4/2005 | Barak | |
| 6,888,351 | B2 | 5/2005 | Belt et al. | |
| 6,889,074 | B2 | 5/2005 | Uber, III et al. | |
| 6,897,658 | B2 | 5/2005 | Belt et al. | |
| 6,906,330 | B2 | 6/2005 | Blevis et al. | |
| D507,832 | S | 7/2005 | Yanniello et al. | |
| 6,915,170 | B2 | 7/2005 | Engleson et al. | |
| 6,915,823 | B2 | 7/2005 | Osborne et al. | |
| 6,917,828 | B2 | 7/2005 | Fukuda | |
| 6,921,384 | B2 | 7/2005 | Reilly et al. | |
| 6,928,142 | B2 | 8/2005 | Shao et al. | |
| 6,935,560 | B2 | 8/2005 | Andreasson et al. | |
| 6,936,030 | B1 | 8/2005 | Pavlik et al. | |
| 6,939,302 | B2 | 9/2005 | Griffiths et al. | |
| 6,940,070 | B2 | 9/2005 | Tumer | |
| 6,943,355 | B2 | 9/2005 | Shwartz et al. | |
| 6,957,522 | B2 | 10/2005 | Baldwin et al. | |

| | | | | | | |
|---|---|---|---|---|---|---|
| 6,958,053 | B1 | 10/2005 | Reilly | 2003/0136912 A1 | 7/2003 | Juni |
| 6,963,770 | B2 | 11/2005 | Scarantino et al. | 2003/0144322 A1 | 7/2003 | Kozikowski et al. |
| 6,970,735 | B2 | 11/2005 | Uber, III et al. | 2003/0147887 A1 | 8/2003 | Wang et al. |
| 6,972,001 | B2 | 12/2005 | Emig et al. | 2003/0158481 A1 | 8/2003 | Stotzka et al. |
| 6,974,443 | B2 | 12/2005 | Reilly et al. | 2003/0183226 A1 | 10/2003 | Brand et al. |
| 6,976,349 | B2 | 12/2005 | Baldwin et al. | 2003/0189174 A1 | 10/2003 | Tanaka et al. |
| 6,984,222 | B1 | 1/2006 | Hitchins et al. | 2003/0191430 A1 | 10/2003 | D'Andrea et al. |
| 6,985,870 | B2 | 1/2006 | Martucci et al. | 2003/0202629 A1 | 10/2003 | Dunham et al. |
| 6,988,981 | B2 | 1/2006 | Hamazaki | 2003/0208117 A1 | 11/2003 | Shwartz et al. |
| 6,994,249 | B2 | 2/2006 | Peterka et al. | 2003/0215122 A1 | 11/2003 | Tanaka |
| 7,011,814 | B2 | 3/2006 | Suddarth et al. | 2003/0215124 A1 | 11/2003 | Li |
| 7,012,430 | B2 | 3/2006 | Misic | 2003/0219149 A1 | 11/2003 | Vailaya et al. |
| 7,017,622 | B2 | 3/2006 | Osborne et al. | 2004/0003001 A1 | 1/2004 | Shimura |
| 7,018,363 | B2 | 3/2006 | Cowan et al. | 2004/0010397 A1 | 1/2004 | Barbour et al. |
| 7,019,783 | B2 | 3/2006 | Kindem et al. | 2004/0015075 A1 | 1/2004 | Kimchy et al. |
| 7,025,757 | B2 | 4/2006 | Reilly et al. | 2004/0021065 A1 | 2/2004 | Weber |
| 7,026,623 | B2 | 4/2006 | Oaknin et al. | 2004/0044282 A1 | 3/2004 | Mixon et al. |
| 7,043,063 | B1 | 5/2006 | Noble et al. | 2004/0051368 A1 | 3/2004 | Caputo et al. |
| 7,103,204 | B1 | 9/2006 | Celler et al. | 2004/0054248 A1 | 3/2004 | Kimchy et al. |
| 7,142,634 | B2 | 11/2006 | Engler et al. | 2004/0054278 A1 | 3/2004 | Kimchy et al. |
| 7,147,372 | B2 | 12/2006 | Nelson et al. | 2004/0065838 A1 | 4/2004 | Tumer |
| 7,164,130 | B2 | 1/2007 | Welsh et al. | 2004/0075058 A1 | 4/2004 | Blevis et al. |
| 7,176,466 | B2 | 2/2007 | Rousso et al. | 2004/0081623 A1 | 4/2004 | Eriksen et al. |
| 7,187,790 | B2 | 3/2007 | Sabol et al. | 2004/0082918 A1 | 4/2004 | Evans et al. |
| 7,217,953 | B2 | 5/2007 | Carlson | 2004/0084340 A1 | 5/2004 | Morelle et al. |
| 7,256,386 | B2 | 8/2007 | Carlson et al. | 2004/0086437 A1 | 5/2004 | Jackson et al. |
| 7,327,822 | B2 | 2/2008 | Sauer et al. | 2004/0101176 A1 | 5/2004 | Mendonca et al. |
| 7,359,535 | B2 | 4/2008 | Salla et al. | 2004/0101177 A1 | 5/2004 | Zahlmann et al. |
| 7,373,197 | B2 | 5/2008 | Daighighian et al. | 2004/0116807 A1 | 6/2004 | Amrami et al. |
| 7,444,010 | B2 | 10/2008 | De Man | 2004/0120557 A1 | 6/2004 | Sabol |
| 7,468,513 | B2 | 12/2008 | Charron et al. | 2004/0122311 A1 | 6/2004 | Cosman |
| 7,490,085 | B2 | 2/2009 | Walker et al. | 2004/0125918 A1 | 7/2004 | Shanmugaval et al. |
| 7,502,499 | B2 | 3/2009 | Grady | 2004/0138557 A1 | 7/2004 | Le et al. |
| 7,570,732 | B2 | 8/2009 | Stanton et al. | 2004/0144925 A1 | 7/2004 | Stoddart et al. |
| 7,592,597 | B2 | 9/2009 | Hefetz et al. | 2004/0153128 A1 | 8/2004 | Suresh et al. |
| 7,620,444 | B2 | 11/2009 | Le et al. | 2004/0162492 A1 | 8/2004 | Kobayashi |
| 7,627,084 | B2 | 12/2009 | Jabri et al. | 2004/0171924 A1 | 9/2004 | Mire et al. |
| 7,672,491 | B2 | 3/2010 | Krishnan et al. | 2004/0183022 A1 | 9/2004 | Weinberg |
| 7,680,240 | B2 | 3/2010 | Manjeshwar et al. | 2004/0184644 A1 | 9/2004 | Leichter et al. |
| 7,705,316 | B2 | 4/2010 | Rousso et al. | 2004/0193453 A1 | 9/2004 | Butterfield et al. |
| 7,826,889 | B2 | 11/2010 | David et al. | 2004/0204646 A1 | 10/2004 | Nagler et al. |
| 7,831,024 | B2 | 11/2010 | Metzler et al. | 2004/0205343 A1 | 10/2004 | Forth et al. |
| 7,835,927 | B2 | 11/2010 | Schlotterbeck et al. | 2004/0210126 A1 | 10/2004 | Hajaj et al. |
| 7,894,650 | B2 | 2/2011 | Weng et al. | 2004/0238743 A1 | 12/2004 | Gravrand et al. |
| 7,968,851 | B2 | 6/2011 | Rousso et al. | 2004/0251419 A1 | 12/2004 | Nelson et al. |
| 2001/0016029 | A1 | 8/2001 | Tumer | 2004/0253177 A1 | 12/2004 | Elmaleh et al. |
| 2001/0020131 | A1 | 9/2001 | Kawagishi et al. | 2005/0001170 A1 | 1/2005 | Juni |
| 2001/0035902 | A1 | 11/2001 | Iddan et al. | 2005/0006589 A1 | 1/2005 | Young et al. |
| 2001/0049608 | A1 | 12/2001 | Hochman | 2005/0020898 A1 | 1/2005 | Vosniak et al. |
| 2002/0068864 | A1 | 6/2002 | Bishop et al. | 2005/0020915 A1 | 1/2005 | Bellardinelli et al. |
| 2002/0072784 | A1 | 6/2002 | Sheppard et al. | 2005/0023474 A1 | 2/2005 | Persyk et al. |
| 2002/0085748 | A1 | 7/2002 | Baumberg | 2005/0029277 A1 | 2/2005 | Tachibana |
| 2002/0087101 | A1 | 7/2002 | Barrick et al. | 2005/0033157 A1 | 2/2005 | Klein et al. |
| 2002/0099295 | A1 | 7/2002 | Gil et al. | 2005/0055174 A1 | 3/2005 | David et al. |
| 2002/0099310 | A1 | 7/2002 | Kimchy et al. | 2005/0056788 A1 | 3/2005 | Juni |
| 2002/0099334 | A1 | 7/2002 | Hanson et al. | 2005/0074402 A1 | 4/2005 | Cagnolini et al. |
| 2002/0103429 | A1 | 8/2002 | DeCharms | 2005/0107698 A1 | 5/2005 | Powers et al. |
| 2002/0103431 | A1 | 8/2002 | Toker et al. | 2005/0107914 A1 | 5/2005 | Engleson et al. |
| 2002/0145114 | A1 | 10/2002 | Inoue et al. | 2005/0108044 A1 | 5/2005 | Koster |
| 2002/0148970 | A1 | 10/2002 | Wong et al. | 2005/0113945 A1 | 5/2005 | Engleson et al. |
| 2002/0165491 | A1 | 11/2002 | Reilly | 2005/0121505 A1 | 6/2005 | Metz et al. |
| 2002/0168094 | A1 | 11/2002 | Kaushikkar et al. | 2005/0131270 A1 | 6/2005 | Weil et al. |
| 2002/0168317 | A1 | 11/2002 | Daighighian et al. | 2005/0148869 A1 | 7/2005 | Masuda |
| 2002/0172405 | A1 | 11/2002 | Schultz | 2005/0149350 A1 | 7/2005 | Kerr et al. |
| 2002/0179843 | A1 | 12/2002 | Tanaka et al. | 2005/0156115 A1 | 7/2005 | Kobayashi et al. |
| 2002/0183645 | A1 | 12/2002 | Nachaliel | 2005/0173643 A1 | 8/2005 | Tumer |
| 2002/0188197 | A1 | 12/2002 | Bishop et al. | 2005/0187465 A1 | 8/2005 | Motomura et al. |
| 2002/0198738 | A1 | 12/2002 | Osborne | 2005/0198800 A1 | 9/2005 | Reich |
| 2003/0001098 | A1 | 1/2003 | Stoddart et al. | 2005/0203389 A1 | 9/2005 | Williams |
| 2003/0001837 | A1 | 1/2003 | Baumberg | 2005/0205792 A1 | 9/2005 | Rousso et al. |
| 2003/0006376 | A1 | 1/2003 | Tumer | 2005/0205796 A1 | 9/2005 | Bryman |
| 2003/0013950 | A1 | 1/2003 | Rollo et al. | 2005/0211909 A1 | 9/2005 | Smith |
| 2003/0013966 | A1 | 1/2003 | Barnes et al. | 2005/0215889 A1 | 9/2005 | Patterson, II |
| 2003/0038240 | A1 | 2/2003 | Weinberg | 2005/0234424 A1 | 10/2005 | Besing et al. |
| 2003/0055685 | A1 | 3/2003 | Cobb et al. | 2005/0247893 A1 | 11/2005 | Fu et al. |
| 2003/0063787 | A1 | 4/2003 | Natanzon et al. | 2005/0253073 A1 | 11/2005 | Joram et al. |
| 2003/0071219 | A1 | 4/2003 | Motomura et al. | 2005/0261936 A1 | 11/2005 | Silverbrook et al. |
| 2003/0081716 | A1 | 5/2003 | Tumer | 2005/0261937 A1 | 11/2005 | Silverbrook et al. |
| 2003/0135388 | A1 | 7/2003 | Martucci et al. | 2005/0261938 A1 | 11/2005 | Silverbrook et al. |

| | | | |
|---|---|---|---|
| 2005/0266074 A1 | 12/2005 | Zilberstein et al. | |
| 2005/0277833 A1 | 12/2005 | Williams, Jr. | |
| 2005/0277911 A1 | 12/2005 | Stewart et al. | |
| 2005/0278066 A1 | 12/2005 | Graves et al. | |
| 2005/0288869 A1 | 12/2005 | Kroll et al. | |
| 2006/0000983 A1 | 1/2006 | Charron et al. | |
| 2006/0033028 A1 | 2/2006 | Juni | |
| 2006/0036157 A1 | 2/2006 | Tumer | |
| 2006/0072799 A1 | 4/2006 | McLain | |
| 2006/0109950 A1 | 5/2006 | Arenson et al. | |
| 2006/0122503 A1 | 6/2006 | Burbank et al. | |
| 2006/0145081 A1 | 7/2006 | Hawman | |
| 2006/0160157 A1 | 7/2006 | Zuckerman | |
| 2006/0237652 A1 | 10/2006 | Kimchy et al. | |
| 2006/0257012 A1 | 11/2006 | Kaufman et al. | |
| 2007/0116170 A1 | 5/2007 | De Man et al. | |
| 2007/0133852 A1 | 6/2007 | Collins et al. | |
| 2007/0156047 A1 | 7/2007 | Nagler et al. | |
| 2007/0166227 A1 | 7/2007 | Liu et al. | |
| 2007/0189436 A1 | 8/2007 | Goto et al. | |
| 2007/0194241 A1 | 8/2007 | Rousso et al. | |
| 2007/0265230 A1 | 11/2007 | Rousso et al. | |
| 2008/0001090 A1 | 1/2008 | Ben-Haim et al. | |
| 2008/0029704 A1 | 2/2008 | Hefetz et al. | |
| 2008/0033291 A1 | 2/2008 | Rousso et al. | |
| 2008/0036882 A1 | 2/2008 | Uemura et al. | |
| 2008/0042067 A1 | 2/2008 | Rousso et al. | |
| 2008/0128626 A1 | 6/2008 | Rousso et al. | |
| 2008/0137938 A1 | 6/2008 | Zahniser | |
| 2008/0230702 A1 | 9/2008 | Rousso et al. | |
| 2008/0230705 A1 | 9/2008 | Rousso et al. | |
| 2008/0237482 A1 | 10/2008 | Shahar et al. | |
| 2008/0260228 A1 | 10/2008 | Dichterman et al. | |
| 2008/0260637 A1 | 10/2008 | Dickman | |
| 2008/0277591 A1 | 11/2008 | Shahar et al. | |
| 2009/0001273 A1 | 1/2009 | Hawman | |
| 2009/0018412 A1 | 1/2009 | Schmitt | |
| 2009/0078875 A1 | 3/2009 | Rousso et al. | |
| 2009/0112086 A1 | 4/2009 | Melman | |
| 2009/0152471 A1 | 6/2009 | Rousso et al. | |
| 2009/0190807 A1 | 7/2009 | Rousso et al. | |
| 2009/0201291 A1 | 8/2009 | Ziv et al. | |
| 2009/0236532 A1 | 9/2009 | Frach et al. | |
| 2009/0304582 A1 | 12/2009 | Rousso et al. | |
| 2010/0006770 A1 | 1/2010 | Balakin | |
| 2010/0021378 A1 | 1/2010 | Rousso et al. | |
| 2010/0102242 A1 | 4/2010 | Burr et al. | |
| 2010/0140483 A1 | 6/2010 | Rousso et al. | |
| 2010/0202664 A1 | 8/2010 | Busch et al. | |
| 2012/0106820 A1 | 5/2012 | Rousso et al. | |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 6-109848 | 4/1994 |
| JP | 06-109848 | 4/1994 |
| JP | 07-059763 | 3/1995 |
| JP | 07-141523 | 6/1995 |
| JP | 08-292268 | 11/1996 |
| JP | 11-072564 | 3/1999 |
| WO | WO 92/00402 | 9/1992 |
| WO | WO 98/16852 | 4/1998 |
| WO | 99/03003 | 1/1999 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | 00/18294 | 4/2000 |
| WO | WO 00/18294 | 4/2000 |
| WO | WO 00/22975 | 4/2000 |
| WO | 00/31522 | 6/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

From Whole-Body Counting to Imaging: The Computer Aided Collimation Gamma Camera Project (CACAO). C. Jeanguillaume; S. Begot; M. Quartuccio; A. Douiri; P. Ballongue. Radiatioin Protection Dosimetry. vol. 89, Nos. 3-4, pp. 349-352, (2000). Nuclear Technology Publishing.

Jeanguillaume et al, "From Whole-Body Counting to Imaging: The Computer Aided Collimation Gamma Camera Project (CACAO)", *Radiation Protection Dosimetry*, 89(3-4):349-352, 2000.

Quartuccio et al, "The Computer Assisted Collimation Gamma Camera: A New Approach to Imaging Contaminated Tissues", *Radiation Protection Dosimetry*, 89(3-4):343-348, 2000.

Lavallée et al. "Building a Hybrid Patient's Model for Augmented Reality in Surgery: A Registration Problem", Computing in Biological Medicine, 25(2): 149-164, 1995. p. 149-150.

Kojima et al. "Quantitative Planar Imaging Method for Measurement of Renal Activity by Using a Conjugate-Emission Image and Transmission Data", Medical Physics, 27(3): 608-615, 2000. p. 608.

Pardridge et al. "Tracer Kinetic Model of Blood-Brain Barrier Transport of Plasma Protein-Bound Ligands", Journal of Clinical Investigation, 74: 745-752, 1984.

Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.

Huesman et al. "Kinetic Parameter Estimation From SPECT Cone-Beam Projection Measurements", Physics in Medicine and Biology, 43(4): 973-982, 1998.

Reutter et al. "Kinetic Parameter Estimation From Attenuated SPECT Projection Measurements", IEEE Transactions on Nuclear Science, 45(6): 3007-3013, 1998.

Official Action Dated Aug. 10, 2007 From the United States Patent and Trademark Office Re.: U.S. Appl. No. 10/836,223.

Official Action Dated May 13, 2009 From the US Patent and Trademark Office Re.: U.S. Appl. No. 11/798,017.

Official Action Dated May 14, 2009 From the US Patent and Trademark Office Re.: U.S. Appl. No. 11/656,548.

Response Dated Mar. 13, 2008 to Official Action of Dec. 13, 2007 From the US Patent and Trademark Office Re.: U.S. Appl. No. 10/616,301.
Response Dated Mar. 15, 2007 to Official Action of Dec. 15, 2006 From the US Patent and Trademark Office Re.: U.S. Appl. No. 10/616,301.
Response Dated Sep. 22, 2008 to Official Action of Jun. 25, 2008 From US Patent and Trademark Office Re.: U.S. Appl. No. 10/616,301.
Response Dated Oct. 31, 2007 to Official Action of Jul. 12, 2007 From the US Patent and Trademark Office Re.: U.S. Appl. No. 10/616,301.
Second International Search Report Dated Jun. 1, 2009 From the International Searching Authority Re.: Application No. PCT/IL07/00918.
Second Written Opinion Dated Jun. 1, 2009 From the International Searching Authority Re.: Application No. PCT/IL07/00918.
Bloch et al. "Application of Computerized Tomography to Radiation Therapy and Surgical Planning", Proceedings of the IEEE, 71(3): 351-355, Mar. 1983.
Final OA dated Jul. 12, 2007.
Invitation to Pay Additional Fees.
Invitation to pay additional fees dated Apr. 18, 2007.
OA dated Sep. 4, 2008.
OA of Jun. 1, 2006.
OA of Aug. 10, 2007.
OA of Jan. 17, 2006.
OA of Jun. 19, 2006.
OA of Dec. 2, 2007.
OA of Jan. 7, 2009.
Official Action Dated May 3, 2007 From the US Patent and Trademark Office Re.: U.S. Appl. No. 10/240,239.
Official Action Dated Oct. 7, 2008 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated Apr. 15, 2008 From the US Patent and Trademark Office Re.: U.S. Appl. No. 09/727,464.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Apr. 20, 2006 From the US Patent and Trademark Office Re.: U.S. Appl. No. 10/240,239.
Official Action Dated Jun. 23, 2006 From the US Patent and Trademark Office Re.: U.S. Appl. No. 09/727,464.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/IL2005/000575.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Hassan et al. "A Radiotelemetry Pill for the Measurement of Ionising Radiation Using a Mercuric Iodide Detector", Physics in Medicine and Biology, 23(2): 302-308, 1978.
Hoffman et al. "Intraoperative Probes and Imaging Probes", European Journal of Nuclear Medicine, 26(8): 913-935, 1999.
Zhang et al. "An Innovative High Efficiency and High Resolution Probe for Prostate Imaging", The Journal of Nuclear Medicine, 68: 18, 2000. Abstract.
Communication Pursuant to Article 96(2) EPC Dated Jun. 19, 2006 From the European Patent Office Re.: Application No. 03810570.6.
Communication pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Search Report Dated Jul. 11, 2008 From the International Searching Authority of the Patent Cooperation Treaty Re.: Application No. PCT/IL06/01511.
International Search Report May 24, 2007 From the International Searching Authority of the Patent Cooperation Treaty Re.: Application No. PCT/IL05/00575.
International Search Report Dated Nov. 1, 2007 From the International Searching Authority of the Patent Cooperation Treaty Re.: Application No. PCT/IL06/00840.
International Search Report Dated Jul. 25, 2008 From the International Searching Authority of the Patent Cooperation Treaty Re.: Application No. PCT/IL2007/001588.
International Search Report Dated Feb. 1, 2006 From the International Scarching Authority of the Patent Cooperation Treaty Re.: Application No. PCT/IL05/00048.
International Search Report Dated Jul. 2, 2007 From the International Searching Authority of the Patent Cooperation Treaty Re.: Application No. PCT/IL2006/001291.
International Search Report Dated Aug. 3, 2006 From the International Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated Mar. 26, 2007 From the International Searching Authority of the Patent Cooperation Treaty Re.: Application No. PCT/IL05/00394.
Official Action Dated Jun. 1, 2006 From the United States Patent and Trademark Office Re.: U.S. Appl. No. 10/686,536.
Official Action Dated Dec. 2, 2007 From the Israeli Patent Office Re.: Application No. 158442.
Official Action Dated May 3, 2007 From the United States Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Jul. 12, 2007 From the US Patent and Trademark Office Re.: U.S. Appl. No. 10/616,301.
Official Action Dated Dec. 15, 2006 From the US Patent Office Re.: U.S. Appl. No. 10/616,301.
Official Action Dated Apr. 15, 2008 From the United States Patent and Trademark Office Re.: U.S. Appl. No. 09/641,973.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Official Action Dated Jan. 17, 2006 From the United States Patent and Trademark Office Re.: U.S. Appl. No. 11/034,007.
Official Action Dated Jul. 17, 2007 From the Israeli Patent Office Re.: Application No. 154323.
Official Action Dated Apr. 20, 2006 From the United States Patent and Trademark Office Re.: U.S. Appl. No. 10/240,239.
Official Action Dated Mar. 21, 2008 From the US Patent and Trademark Office Re.: U.S. Appl. No. 10/533,568.

Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Sep. 30, 2008 From the US Patent and Trademark Office Re.: U.S. Appl. No. 10/616,301.
Supplementary European Search Report Dated Dec. 12, 2005 From the European Patent Office Re.: Application No. 03810570.6.
Supplementary Partial European Search Report Dated Nov. 11, 2008 From the European Patent Office Re.: Application No. 01951883.6.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Oct. 10, 2006 From the International Searching Authority of the Patent Cooperation Treaty Re.: Application No. PCT/IL06/00059.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
International Search Report Sep. 12, 2002 From the International Searching Authority of the Patent Cooperation Treaty Re.: Application No. PCT/IL02/00057.
Piperno et al. "Breast Cancer Screening by Impedance Measurements", Frontiers Med. Biol. Engng., 2(2): 11-17, 1990.
Rajshekhar "Continuous Impedance Monitoring During CT-Guided Stereotactic Surgery: Relative Value in Cystic and Solid Lesions", British Journal of Neurosurgery, 6: 439-444, 1992.
Jessup "Tumor Markers—Prognostic and Therapeutic Implications for Colorectal Carcinoma", Surgical Oncology, 7: 139-151, 1998.
Corstens et al. "Nuclear Medicine's Role in Infection and Inflamation", The Lancet, 354: 765-770, 1999.
Mori et al. "Overexpression of Matrix Metalloproteinase-7mRNA in Human Colon Carcinomas", Cancer, 75: 1516-1519, 1995.
Erbil et al. "Use and Limitations of Serum Total and Lipid-Bound Sialic Acid Concentrations as Markers for Colorectal Cancer", Cancer, 55: 404-409, 1985.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Day et al. "Localization of Radioiodinated Rat Fibrogen in Transplanted Rat Tumors", J. Nat. Cancer Inst., 23: 799-812, 1959.
Communication Pursuant to Article 94(3) EPC Dated Oct. 21, 2009 From the European Patent Office Re.: Application No. 02716285.8.
Notice of Allowance Dated Sep. 17, 2009 From the US Patent and Trademark Office Re.: U.S. Appl. No. 10/533,568.
Official Action Dated Sep. 1, 2009 From the US Patent and Trademark Office Re.: U.S. Appl. No. 11/794,799.

Official Action Dated Sep. 2, 2009 From the US Patent and Trademark Office Re.: U.S. Appl. No. 10/343,792.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Sep. 16, 2009 From the US Patent and Trademark Office Re.: U.S. Appl. No. 09/727,464.
Official Action Dated Sep. 21, 2009 From the US Patent and Trademark Office Re.: U.S. Appl. No. 11/798,017.
Official Action Dated Aug. 28, 2009 From the US Patent and Trademark Office Re.: U.S. Appl. No. 10/240,239.
Official Action Dated Oct. 30, 2009 From the US Patent and Trademark Office Re.: U.S. Appl. No. 11/980,690.
Response Dated Dec. 10, 2009 to Official Action of Aug. 11, 2009 From the US Patent and Trademark Office Re.: U.S. Appl. No. 09/641,973.
Response Dated Oct. 12, 2009 to Notice of Allowance of Jul. 16, 2009 From the US Patent and Trademark Office Re.: U.S. Appl. No. 12/084,559.
Response Dated Oct. 14, 2009 to Official Action of May 14, 2009 From the US Patent and Trademark Office Re.: U.S. Appl. No. 11/656,548.
Response Dated Nov. 16, 2009 to Official Action of Jul. 15, 2009 From the US Patent and Trademark Office Re.: U.S. Appl. No. 10/616,301.
Supplementary Partial European Search Report and the European Search Opinion Dated Oct. 16, 2009 From the European Patent Office Re.: Application No. 06756259.5.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Qi et al. "Resolution and noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Communication Pursuant to Article 94(3) EPC Dated Jul. 22, 2009 From the European Patent Office Re.: Application No. 06809851.6.
Notice of Allowance Dated Jul. 16, 2009 From the US Patent and Trademark Office Re.: U.S. Appl. No. 12/084,559.
Official Action Dated Jul. 7, 2009 From the US Patent and Trademark Office Re.: U.S. Appl. No. 10/533,568.
Official Action Dated Jul. 15, 2009 From the US Patent and Trademark Office Re.: U.S. Appl. No. 10/616,301.
Official Action Dated Jul. 20, 2009 From the US Patent and Trademark Office Re.: U.S. Appl. No. 11/980,617.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Wu et al. "ECG-Gated Pinhole SPECT in Mice With Millimeter Spatial Resolution", IEEE Transactions on Nuclear Science, 47(3): 1218-1221, Jun. 2000.
Appeal Brief Dated Jan. 19, 2010 to Notice of Appeal of Nov. 16, 2009 From the US Patent and Trademark Office Re.: U.S. Appl. No. 10/616,301.
Notice of Allowance Dated Nov. 23, 2009 From the US Patent and Trademark Office Re.: U.S. Appl. No. 12/084,559.
Notice of Appeal and Pre-Appeal Brief Dated Jan. 4, 2010 to Official Action of Sep. 2, 2009 From the US Patent and Trademark Office Re.: U.S. Appl. No. 10/343,792.
Official Action Dated Mar. 1, 2010 From the US Patent and Trademark Office Re.: U.S. Appl. No. 11/794,799.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.

Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Mar. 11, 2010 From the US Patent and Trademark Office Re.: U.S. Appl. No. 11/607,075.
Response Dated Jan. 14, 2010 to Official Action of Sep. 15, 2009 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/836,223.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Supplementary Partial European Search Report and the European Search Opinion Dated Dec. 15, 2009 From the European Patent Office Re.: Application No. 06832278.3.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Kadrmas et al. "Static Versus Dynamic Teboroxime Myocardial Perfusion SPECT in Canines", IEEE Transactions on Nuclear Science, 47(3): 1112-1117, Jun. 2000.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First col., 2nd §.
Communication Pursuant to Article 94(3) EPC Dated Mar. 8, 2010 From the European Patent Office Re.: Application No. 06832278.3.
Official Action Dated Mar. 19, 2010 From the US Patent and Trademark Office Re.: U.S. Appl. No. 10/240,239.
International Search Report Dated Oct. 10, 2006 From the International Searching Authority of the Patent Cooperation Treaty Re.: Application No. PCT/IL06/00059.
Written Opinion Dated Aug. 3, 2006 From the International Searching Authority of the Patent Cooperation Treaty Re.: Application No. PCT/IL05/001173.
Official Action Dated Apr. 9, 2010 From the US Patent and Trademark Office Re.: U.S. Appl. No. 11/798,017.
Communication Pursuant to Article 93(3) EPC Dated Mar. 8, 2010 From the European Patent Office Re.: Application No. 06832278.3.
Official Action Dated Apr. 8, 2010 From the US Patent and Trademark Office Re.: U.S. Appl. No. 11/980,690.
Official Action Dated Apr. 28, 2010 From the US Patent and Trademark Office Re.: U.S. Appl. No. 10/616,301.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.

Response Dated May 11, 2010 to Official Action of Mar. 11, 2010 From the US Patent and Trademark Office Re.: U.S. Appl. No. 11/607,075.
Response Dated May 26, 2010 to Official Action of Mar. 19, 2010 From the US Patent and Trademark Office Re.: U.S. Appl. No. 10/240,239.
Communication Pursuant to Article 94(3) EPC Dated Apr. 16, 2010 From the European Patent Office Re. Application No. 01951883.6.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response Dated Jul. 8, 2010 to Communication Pursuant to Article 94(3) EPC of Mar. 8, 2010 From the European Patent Office Re.: Application No. 06832278.3.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Response Dated Jul. 1, 2010 to Official Action of Mar. 2, 2010 From the US Patent and Trademark Office Re.: U.S. Appl. No. 10/836,223.
Response Dated Jul. 8, 2010 to Official Action of Apr. 9, 2010 From the US Patent and Trademark Office Re.: U.S. Appl. No. 11/798,017.
Official Action Dated Jul. 27, 2010 From the US Patent and Trademark Office Re.: U.S. Appl. No. 10/616,307.
Response Dated Jul. 26, 2010 to Official Action of Apr. 28, 2010 From the US Patent and Trademark Office Re.: U.S. Appl. No. 10/616,301.
Notice of Allowance Dated Jun. 30, 2010 From the United States Patent and Trademark Office Re.: U.S. Appl. No. 09/727,464.
Official Action Dated Aug. 3, 2010 From the US Patent and Trademark Office Re.: U.S. Appl. No. 11/980,690.
Supplemental Response After Interview Dated Aug. 4, 2010 to Official Action of Mar. 2, 2010 From the US Patent and Trademark Office Re.: U.S. Appl. No. 11/980,617.
Notice of Allowance Dated Jul. 22, 2010 From the US Patent and Trademark Office Re.: U.S. Appl. No. 11/794,799.
Response Dated Aug. 16, 2010 to Communication Pursuant to Article 94(3) EPC of Apr. 16, 2010 From the European Patent Office Re. Application No. 01951883.6.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Response Dated Aug. 25, 2010 to Official Action of Jul. 27, 2010 From the US Patent and Trademark Office Re.: U.S. Appl. No. 10/616,307.
Communication Pursuant to Article 94(3) EPC Dated May 12, 2010 From the European Patent Office Re.: Application No. 06809851.6.
Notice of Allowance Dated Aug. 25, 2010 From the US Patent and Trademark Office Re. U.S. Appl. No. 11/980,617.
Response Dated Sep. 8, 2010 to Communication Pursuant to Article 94(3) EPC Dated May 12, 2010 From the European Patent Office Re.: Application No. 06809851.6.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Response dated Sep. 1, 2010 to Official Action of Aug. 3, 2010 From the US Patent and Trademark Office Re.: U.S. Appl. No. 11/980,690.
Official Action Dated Sep. 30, 2010 From the US Patent and Trademark Office Re.: U.S. Appl. No. 11/798,017.
Response Dated Oct. 5, 2010 to Official Action of Jul. 19, 2010 From the US Patent and Trademark Office Re.: U.S. Appl. No. 11/656,548.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Brown et al. "Method for Segmenting Chest CT Image Data Using an Anatomical Model: Preliminary Results", IEEE Transactions on Medical Imaging, 16(6): 828-839, Dec. 1997.

Del Guerra et al. "An Integrated PET-SPECT Small Animal Imager: Preliminary Results", Nuclear Science Symposium, IEEE Records, 1: 541-544, 1999.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Official Action Dated Jan. 31, 2011 From the US Patent and Trademark Office Re. U.S. Appl. No. 11/667,793.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Communication Pursuant to Article 94(3) EPC Dated Mar. 2, 2011 From the European Patent Office Re.: Application No. 06756259.5.
International Search Report Dated Sep. 12, 2002 From the International Searching Authority of the Patent Cooperation Treaty Re: Application No. PCT/IL02/00057.
International Search Report Dated May 24, 2007 From the International Searching Authority of the Patent Cooperation Treaty Re.: Application No. PCT/IL05/00575.
Notice of Allowance Dated Nov. 15, 2010 From the US Patent and Trademark Office Re. U.S. Appl. No. 10/616,301.
Notice of Appeal Dated Nov. 16, 2009 to Official Action of Jul. 15, 2009 From the US Patent and Trademark Office Re.: U.S. Appl. No. 10/616,301.
Notice of Non-Compliant Amendment Dated Feb. 14, 2011 From the US Patent and Trademark Office Re.: U.S. Appl. No. 10/616,307.
Office Action Dated Dec. 2, 2007 From the Israeli Patent Office Re.: Application No. 158442.
Official Action Dated Jun. 1, 2006 From the US Patent and Trademark Office Re.: U.S. Appl. No. 10/686,536.
Official Action Dated Nov. 1, 2010 From the US Patent and Trademark Office Re.: U.S. Appl. No. 11/980,690.

Official Action Dated Sep. 5, 2002 From the US Patent and Trademark Office Re.: U.S. Appl. No. 12/084,559.
Official Action Dated Aug. 10, 2007 From the US Patent and Trademark Office Re.: U.S. Appl. No. 10/836,223.
Official Action Dated Mar. 15, 2004 From the US Patent and Trademark Office Re.: U.S. Appl. No. 09/765,316.
Response Dated Mar. 8, 2011 to Official Action of Dec. 8, 2010 From the US Patent and Trademark Office Re.: U.S. Appl. No. 11/980,690.
Response Dated Feb. 10, 2011 to Notice of Allowance of Nov. 15, 2010 From the US Patent and Trademark Office Re. U.S. Appl. No. 10/616,301.
Written Opinion Dated Jul. 2, 2007 From the International Searching Authority of the Patent Cooperation Treaty Re.: Application No. PCT/IL2006/001291.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Hayakawa et al. "A PET-MRI Registration Technique for PET Studies of the Rat Brain", Nuclear Medicine & Biology, 27: 121-125, 2000. p. 121, col. 1.
Jeanguillaume et al. "From the Whole-Body Counting to Imaging: The Computer Aided Collimation Gamma Camera Project (CACAO)", Radiation Projection Dosimetry, 89(3-4): 349-352, 2000. & RSNA 2000 Infosystem, 87th Scientific Assembly and Annual Meeting, Chicago, Illinois, 2000.
Lavall?e et al. "Building a Hybrid Patient's Model for Augmented Reality in Surgery: A Registration Problem", Computing in Biological Medicine, 25(2): 149-164, 1995.
Lin et al. "Improved Sensor Pills for Physiological Monitoring", NASA Technical Brief, JPL New Technology Report, NPO-20652, 25(2), 2000.
Pluim et al. "Image Registration by Maximization of Combined Mutual Information and Gradient Information", IEEE Transactions on Medical Imaging, 19(8): 1-6, 2000.
Quartuccia et al. "Computer Assisted Collimation Gama Camera: A New Approach to Imaging Contaminated Tissues", Radiation Projection Dosimetry, 89(3-4): 343-348, 2000.
Mettler et al. "Legal Requirements and Radiation Safety", Essentials of Nuclear Medicine Imaging, 2nd Ed., Chap. 13: 323-331, 1985.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Interview Summary Dated May 31, 2011 From the US Patent and Trademark Office Re. U.S. Appl. No. 10/616,301.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "Tc-99m Sestamibi Uptake in Metastatic Prostate Carcinoma", Clinical Nuclear Medicine, XP009145398, 25(2): 133-134, Feb. 2000.
Response Dated Mar. 3, 2011 to Notice of Non-Compliant Amendment of Feb. 14, 2011 From the US Patent and Trademark Office Re.: U.S. Appl. No. 10/616,307.
Notice of Allowance Dated May 5, 2011 From the US Patent and Trademark Office Re.: U.S. Appl. No. 10/240,239.
Notice of Allowance Dated Dec. 17, 2010 From the US Patent and Trademark Office Re. U.S. Appl. No. 11/980,617.
Official Action Dated Dec. 28, 2010 From the US Patent and Trademark Office Re.: U.S. Appl. No. 11/607,075.

Response Dated Dec. 15, 2010 to Official Action of Jul. 19, 2010 From the US Patent and Trademark Office Re.: U.S. Appl. No. 11/656,548.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Notice of Allowance Dated Oct. 11, 2011 From the US Patent and Trademark Office Re. U.S. Appl. No. 11/988,926.
Response Dated Oct. 14, 2011 to Communication Pursuant to Rules 70(2) and 70a(2) EPC of Apr. 4, 2011 From the European Patent Office Re. Application No. 05803689.8.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Communication Pursuant to Article 94(3) EPC Dated Nov. 18, 2011 From the European Patent Office Re. Application No. 05803689.8.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Nov. 28, 2011 to Official Action of Jun. 28, 2011 From the US Patent and Trademark Office Re. U.S. Appl. No. 11/628,074.
Official Action Dated Dec. 15, 2011 From the US Patent and Trademark Office Re.: U.S. Appl. No. 10/343,792.
Official Action Dated Dec. 20, 2011 From the US Patent and Trademark Office Re. U.S. Appl. No. 12/309,479.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion SPECT With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Official Action Dated Jun. 28, 2011 From the US Patent and Trademark Office Re. U.S. Appl. No. 11/628,074.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Communication Pursuant to Article 94(3) EPC Dated Sep. 22, 2011 From the European Patent Office Re. Application No. 06756258.7.
Notice of Allowance Dated Sep. 16, 2011 From the US Patent and Trademark Office Re.: U.S. Appl. No. 11/607,075.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Official Action Dated Sep. 13, 2011 From the US Patent and Trademark Office Re. U.S. Appl. No. 11/976,852.

Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Response Dated Oct. 14, 2011 to Supplementary European Search Report and the European Search Opinion of Mar. 16, 2011 From the European Patent Office Re. Application No. 05803689.8.
Restriction Official Action Dated Nov. 8, 2011 From the US Patent and Trademark Office Re. U.S. Appl. No. 12/309,479.
Response Dated Dec. 8, 2011 to Restriction Official Action of Nov. 8, 2011 From the US Patent and Trademark Office Re. U.S. Appl. No. 12/309,479.
Notice of Allowance Dated Jun. 23, 2011 From the US Patent and Trademark Office Re.: U.S. Appl. No. 10/616,301.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Communication Pursuant to Article 94(3) EPC Dated Nov. 12, 2012 From the European Patent Office Re. Application No. 06756258.7.
Notice of Allowance Dated Nov. 15, 2012 From the US Patent and Trademark Office Re.: U.S. Appl. No. 11/980,683.
Supplementary European Search Report and the European Search Opinion Dated Nov. 13, 2012 From the European Patent Office Re. Application No. 06728347.3.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Official Action Dated Dec. 19, 2012 From the US Patent and Trademark Office Re. U.S. Appl. No. 12/448,473.
Notice of Allowance Dated Oct. 26, 2012 From the US Patent and Trademark Office Re. U.S. Appl. No. 12/514,785.
Official Action Dated Nov. 30, 2012 From the US Patent and Trademark Office Re. U.S. Appl. No. 12/514,785.

US 8,489,176 B1

Page 12

Notice of Allowance Dated Feb. 2, 2012 From the US Patent and Trademark Office Re. U.S. Appl. No. 11/628,074.
Notice of Panel Decision From Pre-Appeal Brief Review Dated Feb. 29, 2012 From the US Patent and Trademark Office Re.: U.S. Appl. No. 10/836,223.
Official Action Dated Mar. 1, 2012 From the US Patent and Trademark Office Re.: U.S. Appl. No. 10/616,307.
Official Action Dated Mar. 6, 2012 From the US Patent and Trademark Office Re. U.S. Appl. No. 12/792,856.
Official Action Dated Apr. 16, 2012 From the US Patent and Trademark Office Re.: U.S. Appl. No. 10/836,223.
Restriction Official Action Dated Mar. 9, 2012 From the US Patent and Trademark Office Re. U.S. Appl. No. 11/976,852.
Restriction Official Action Dated Apr. 13, 2012 From the US Patent and Trademark Office Re. U.S. Appl. No. 11/989,223.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Official Action Dated Aug. 31, 2012 From the US Patent and Trademark Office Re. U.S. Appl. No. 11/980,653.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.
Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanki "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Official Action Dated Oct. 11, 2012 From the US Patent and Trademark Office Re. U.S. Appl. No. 11/976,852.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Official Action Dated Oct. 10, 2012 From the US Patent and Trademark Office Re. U.S. Appl. No. 11/798,017.
Communication Pursuant to Article 94(3) EPC Dated Jun. 11, 2012 From the European Patent Office Re.: Application No. 06756259.5.
Communication Pursuant to Article 94(3) EPC Dated Sep. 23, 2011 From the European Patent Office Re.: Application No. 06832278.3.
Communication Pursuant to Article 94(3) EPC Dated May 29, 2012 From the European Patent Office Re. Application No. 05803689.8.
Communication Under Rule 71(3) EPC Dated May 30, 2012 From the European Patent Office Re.: Application No. 02716285.8.
Examination Report Dated Jun. 22, 2011 From the Government of India, Patent Office, Intellectual Property Building Re. Application No. 2963/CHENP/2006.
International Preliminary Report on Patentability Dated Apr. 7, 2009 From the International Bureau of WIPO Re. Application No. PCT/IL2007/000918.

International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Search Report Dated Jul. 1, 2008 From the international Searching Authority of the Patent Cooperation Treaty Re.: Application No. PCT/IL06/00834.
International Search Report Dated Jul. 2, 2007 From the International Searching Authority Re. Application No. PCT/IL2006/001291.
International Search Report Dated Aug. 3, 2006 From the International Searching Authority Re. Application No. PCT/IL2005/001173.
International Search Report Dated Oct. 15, 2008 From the International Searching Authority Re.: Application No. PCT/IL07/00918.
Notice of Allowance Dated Feb. 23, 2011 From the US Patent and Trademark Office Re.: U.S. Appl. No. 12/728,383.
Official Action Dated Nov. 1, 2010 From the US Patent and Trademark Office Re. U.S. Appl. No. 12/728,383.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Official Action Dated Aug. 13, 2008 From the US Patent and Trademark Office Re. U.S. Appl. No. 11/769,826.
Official Action Dated Feb. 16, 2012 From the US Patent and Trademark Office Re. U.S. Appl. No. 11/747,378.
Official Action Dated May 18, 2012 From the US Patent and Trademark Office Re. U.S. Appl. No. 11/989,223.
Official Action Dated Jun. 21, 2012 From the US Patent and Trademark Office Re. U.S. Appl. No. 12/309,479.
Official Action Dated Jul. 30, 2012 From the US Patent and Trademark Office Re.: U.S. Appl. No. 11/980,683.
Response Dated Apr. 7, 2009 to Official Action of Oct. 7, 2008 From the US Patent and Trademark Office Re.: U.S. Appl. No. 10/616,301.
Response Dated Jan. 27, 2011 to Official Action of Nov. 1, 2010 From the US Patent and Trademark Office Re.: U.S. Appl No. 12/728,383.
Written Opinion Dated Nov. 1, 2007 from the International Searching Authority of the Patent Cooperation Treaty Re.: Application No. PCT/IL06/00840.
Written Opinion Dated Jul. 11, 2008 from the International Searching Authority of the Patent Cooperation Treaty Re.: Application No. PCT/IL06/01511.
Berman et al. "Dual-Isotope Myocardial Perfusion SPECT With Rest Thallium-201 and Stress Tc-99m Sestamibi", Nuclear Cardiology, 12(2): 261-270, May 1994.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Chengazi et al. "Imaging Prostate Cancer With Technetium-99m-7E11-C5.3 (CYT-351)", Journal of Nuclear Medicine, 38: 675-682, 1997.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dillman "Radiolabeled Anti-CD20 Monoclonal Antibodies for the Treatment of B-Cell Lymphoma", Journal of Clinical Oncology, 20(16): 3545-3557, Aug. 15, 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.

Mallinckrodt "Kit for the Preparation of Technetium Tc 99m Sestamibi Injection", Mallinckrodt Inc., Product Sheet, 2 P., Sep. 8, 2008.

Mallinckrodt "OctrcoScan®: Kit for the Preparation of Indium In-111 Pentetreotide. Diagnostic—for Intravenous Use. Rx Only", Mallinckrodt Inc., Product Sheet, 2 P., Oct. 25, 2006.

McJilton et al. "Protein Kinase C? Interacts With Bax and Promotes Survival of Human Prostate Cancer Cells", Oncogene, 22; 7958-7968, 2003.

Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.

Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.

Sands et al. "Methods for the Study of the Metabolism of Radiolabeled Monoclonal Antibodies by Liver and Tumor", The Journal of Nuclear Medicine, 28: 390-398, 1987.

Trikha et al. "Monoclonal Antibodies as Therapeutics in Oncology", Current Opinion in Biotechnology, 13: 609-614, 2002.

Volkow et al. "Imaging the Living Human Brain: Magnetic Resonance Imaging and Positron Emission Tomography", Proc. Natl. Acad. Sci. USA, 94: 2787-2788, Apr. 1997.

International Preliminary Report on Patentability Dated Jan. 22, 2009 From the International Bureau of WIPO Re.: Application No. PCT/IL2006/000834.

International Preliminary Report on Patentability Dated Jan. 22, 2009 From the International Bureau of WIPO Re.: Application No. PCT/IL2006/001511.

International Preliminary Report on Patentability Dated May 22, 2007 From the International Preliminary Examining Authority Re.: Application No. PCT/IL06/00059.

International Preliminary Report on Patentability Dated May 22, 2008 From the International Bureau of WIPO Re.: Application No. PCT/IL2006/001291.

International Preliminary Report on Patentability Dated May 24, 2007 From the International Bureau of WIPO Re.: Application No. PCT/IL2005/001173.

International Preliminary Report on Patentability Dated Apr. 26, 2007 From the International Bureau of WIPO Re.: Application No. PCT/IL2005/000394.

International Preliminary Report on Patentability Dated Jan. 31, 2008 From the International Bureau of WIPO Re.: Application No. PCT/IL2006/000840.

Invitation to Pay Additional Fees Dated Jul. 10, 2008 From the International Searching Authority Re.: Application No. PCT/IL06/01511.

Invitation to Pay Additional Fees Dated Feb. 15, 2007 From the International Searching Authority Re.: Application No. PCT/IL05/00575.

Office Action Dated Jan. 2, 2006 From the Israeli Patent Office Re.: Application No. 154323.

Office Action Dated Sep. 4, 2007 From the Israeli Patent Office Re.: Application No. 157007.

Office Action Dated Jul. 17, 2007 From the Israeli Patent Office Re.: Application No. 154323.

Official Action Dated Jan. 7, 2009 From the US Patent and Trademark Office Re.: U.S. Appl. No. 10/616,307.

Official Action Dated Dec. 16, 2008 From the US Patent and Trademark Office Re.: U.S. Appl. No. 10/343,792.

Official Action Dated Dec. 23, 2008 From the US Patent and Trademark Office Re.: U.S. Appl. No. 09/727,464.

Official Action Dated Nov. 26, 2008 From the US Patent and Trademark Office Re.: U.S. Appl. No. 10/240,239.

Official Action Dated Apr. 29, 2009 From the US Patent and Trademark Office Re.: U.S. Appl. No. 11/980,690.

Response Dated Aug. 14, 2008 to Official Action of Apr. 15, 2008 From the US Patent and Trademark Office Re.: U.S. Appl. No. 09/727,464.

Response Dated Nov. 25, 2005 to Office Action of May 13, 2005 From the Patent Office of the People's Republic of China Re.: Application No. 1817689.5.

Response to the International Search Report and the Written Opinion of Oct. 10, 2006 From the International Searching Authority Re.: Appliction No. PCT/IL06/00059.

Summons to Attend Oral Proceedings Pursuant to Rule 115(1) EPC Dated Jan. 16, 2009 From the European Patent Office Re.: Application No. 03810570.6.

Supplementary Partial European Search Report Dated Sep. 4, 2007 From the European Patent Office Re.: Application No. 0 2716285.8.

Supplementary Partial European Search Report Dated Nov. 20, 2007 From the European Patent Office Re.: Application No. 02716285.8.

Translation of Office Action Dated May 13, 2005 From the Patent Office of the People's Republic of China Re.: Application No. 01817689.5.

Written Opinion Dated Oct. 15, 2008 From the International Searching Authority Re.: Application No. PCT/IL07/00918.

Kinahan et al. "Attenuation Correction for A Combined 3D PET/CT Scanner", Medical Physics, 25(10): 2046-2053, Oct. 1998.

Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.

Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.

Zaidi et al. "Magenetic Resonance Imaging-Guided Attenuation and Scatter Corrections in Three-Dimensional Brain Positron Emission Tomography", Medical Physics, 30(5): 937-948, May 2003.

Zaidi et al. "MRI-Guided Attenuation Correction in 3D Brain PET", Neuroimage Human Brain Mapping 2002 Meeting, 16(2): Abstract 504, Jun. 2002.

Summons to Attend Oral Proceedings Pursuant to Rule 115(1) EPC Dated Nov. 29, 2012 From the European Patent Office Re. Application No. 06756259.5.

Restriction Official Action Dated Aug. 16, 2012 From the US Patent and Trademark Office Re. U.S. Appl. No. 12/448,473.

Notice of Allowance Dated Dec. 26, 2012 From the US Patent and Trademark Office Re.: U.S. Appl. No. 11/980,690.

Official Action Dated Dec. 28, 2012 From the US Patent and Trademark Office Re.: U.S. Appl. No. 10/343,792.

Charland et al. "The Use of Deconvolution and Total Least Squares in Recovering a Radiation Detector Linc Spread Function", Medical Physics, 25(2): 152-160, Feb. 1998. Abstract Only!

Communication Pursuant to Article 94(3) EPC Dated Oct. 26, 2012 From the European Patent Office Re. Application No. 05803689.8.

Official Action Dated Nov. 30, 2012 From the US Patent and Trademark Office Re. U.S. Appl. No. 11/989,223.

* cited by examiner

RADIOACTIVE EMISSION DETECTOR EQUIPPED WITH A POSITION TRACKING SYSTEM AND UTILIZATION THEREOF WITH MEDICAL SYSTEMS AND IN MEDICAL PROCEDURES

FIELD AND BACKGROUND OF THE INVENTION

The present invention relates to a radioactive emission detector equipped with a position tracking system. More particularly, the present invention relates to the functional integration of a radioactive emission detector equipped with a position tracking system as above with medical three-dimensional imaging modalities and/or with guided minimal-invasive surgical instruments. The present invention is therefore useful for calculating the position of a concentrated radiopharmaceutical in the body in positional context of imaged portions of the body, which information can be used, for example, for performing an efficient minimally invasive surgical procedure.

The use of minimally invasive surgical techniques has dramatically affected the methods and outcomes of surgical procedures. Physically cutting through tissue and organs to visually expose surgical sites in conventional "open surgical" procedures causes tremendous blunt trauma and blood loss. Exposure of internal tissues and organs in this manner also dramatically increases the risk of infection. Trauma, blood loss, and infection all combine to extend recovery times, increase the rate of complications, and require a more intensive care and monitoring regiment. The result of such open surgical procedures is more pain and suffering, higher procedural costs, and greater risk of adverse outcomes.

In contrast, minimally invasive surgical procedures cause little blunt trauma or blood loss and minimize the risk of infection by maintaining the body's natural barriers to infection substantially intact. Minimally invasive surgical procedures result in faster recoveries and cause fewer complications than conventional surgical procedures. Minimally invasive procedures, such as laparoscopic, endoscopic, or cystoscopic surgery, have replaced more invasive surgical procedures in all areas of medicine. Due to technological advancements in areas such as fiber optics, micro-tool fabrication, imaging and material science, the physician performing the operation has easier-to-operate and more cost effective tools for use in minimally invasive procedures. However, there still exist a host of technical hurdles that limit the efficacy and increase the difficulty of minimally invasive procedures, some of which were overcame by the development of sophisticated imaging techniques. As is further detailed below the present invention offers a yet further advantage in this respect.

The manipulation of soft tissue organs requires visualization techniques such as computerized tomography (CT), fluoroscopy (X-ray fluoroscopy), magnetic resonance imaging (MRI), optical endoscopy, mammography or ultrasound which distinguish the borders and shapes of soft tissue organs or masses. Over the years, medical imaging has become a vital part in the early detection, diagnosis and treatment of cancer and other diseases. In some cases medical imaging is the first step in preventing the spread of cancer through early detection and in many cases medical imaging makes it possible to cure or eliminate the cancer altogether via subsequent treatment.

An evaluation of the presence or absence of tumor metastasis or invasion has been a major determinant for the achievement of an effective treatment for cancer patients. Studies have determined that about 30% of patients with essentially newly diagnosed tumor will exhibit clinically detectable metastasis. Of the remaining 70% of such patients who are deemed "clinically free" of metastasis, about one-half are curable by local tumor therapy alone. However some of these metastasis or even early stage primary tumors do not show with the imaging tools described above. Moreover often enough the most important part of a tumor to be biopsed or surgically removed is the active, i.e., growing part, whereas using only conventional imaging cannot distinguish this specific part of a tumor from other parts thereof and/or adjacent non affected tissue.

A common practice in order to locate this active part is to mark it with radioactivity tagged materials generally known as radiopharmaceuticals, which are administered orally or intravenously and which tend to concentrate in such areas, as the uptake of such radiopharmaceuticals in the active part of a tumor is higher and more rapid than in the neighboring tumor tissue. Thereafter, a radiation emission detector, typically an invasive detector, is employed for locating the position of the active area.

Medical imaging is often used to build computer models which allow doctors to, for example, guide exact radiation in the treatment of cancer, and to design minimal invasive or open surgical procedures. Moreover, imaging modalities are also used to guide surgeons to the target area inside the patient's body, in the operation room during the surgical procedure. Such procedures may include, for example, biopsies, inserting a localized radiation source for direct treatment of a cancerous lesion, known as brachytherapy (so as to prevent radiation damage to tissues near the lesion), injecting a chemotherapy agent into the cancerous site or removing a cancerous or other lesions.

The aim of all such procedures is to pin-point the target area as precisely as possible in order to get the most precise biopsy results, preferably from the most active part of a tumor, or to remove such a tumor in it's entirety on the one hand with minimal damage to the surrounding, non affected tissues, on the other hand.

However, in the current state of the prior art this goal is yet to be achieved, most of the common imaging modalities such as fluoroscopy, CT, MRI, mammography or ultrasound demonstrate the position and appearance of the entire lesion with anatomical modifications that the lesion causes to it's surrounding tissue, without differentiating between the non-active mass from the physiologically active part thereof.

On the other hand, prior art radiation emission detectors and/or biopsy probes, while being suitable for identifying the location of the radiation site, they leave something to be desired from the standpoint of facilitating the removal or other destruction of the detected cancerous tissue with minimum invasion of the patient.

The combination of modalities, as is offered by the present invention, can reduce the margin of error in positioning such tumors. In addition, the possibility of demonstrating the position of the active part of a tumor superimposed on a scan from an imaging modality that shows the organ or tumor, coupled with the possibility to follow a surgical tool in reference to the afflicted area during a surgical procedure will allow for a more precise and controlled surgical procedures to take place, minimizing the aforementioned problems.

The present invention addresses these and other issues which are further elaborated herein below, and offers physicians and patients more reliable targeting, that in turn will result in less invasive and less destructive surgical procedures.

SUMMARY OF THE INVENTION

According to one aspect of the present invention there is provided a system for calculating a position of a radioactivity emitting source in a system-of-coordinates, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for calculating the position of the radioactivity emitting source in the system-of-coordinates.

According to another aspect of the present invention there is provided a method for defining a position of a radioactivity emitting source in a system-of-coordinates, the method comprising the steps of (a) providing a radioactive emission detector being connected to or communicating with a position tracking system; and (b) monitoring radioactivity being emitted from the radioactivity emitting source, while at the same time, monitoring the position of the radioactive emission detector in the system-of-coordinates, thereby defining the position of the radioactivity emitting source in the system-of-coordinates.

According to yet another aspect of the present invention there is provided a system for calculating a position of a radioactivity emitting source in a first system-of-coordinates and further of projecting the position of the radioactivity emitting source onto a second system-of-coordinates, the system comprising (a) a radioactive emission detector; (b) a position tracking system being connected to and/or communicating with the radioactive emission detector; and (c) a data processor being designed and configured for (i) receiving data inputs from the position tracking system and from the radioactive emission detector; (ii) calculating the position of the radioactivity emitting source in the first system-of-coordinates; and (iii) projecting the position of the radioactivity emitting source onto the second system-of-coordinates.

According to still another aspect of the present invention there is provided a method for calculating a position of a radioactivity emitting source in a first system-of-coordinates and for projecting the position of the radioactivity emitting source onto a second system-of-coordinates, the method comprising the steps of (a) providing a radioactive emission detector being connected to or communicating with a position tracking system; and (b) monitoring radioactivity being emitted from the radioactivity emitting source, while at the same time, monitoring the position of the radioactive emission detector in the first system-of-coordinates, thereby defining the position of the radioactivity emitting source in the first system-of-coordinates and projecting the position of the radioactivity emitting source onto the second system-of-coordinates.

According to an additional aspect of the present invention there is provided a system for calculating a position of a body component and a position of a radiopharmaceutical uptaking portion of the body component within a subject, the system comprising (a) a three-dimensional imaging modality being connected to and/or communicating with a first position tracking system for calculating the position of the body component in a first system-of-coordinates; (b) a radioactive emission detector being connected to and/or communicating with a second position tracking system for tracking a position of the radiopharmaceutical uptaking portion of the body component in a second system-of-coordinates; and (c) at least one data processor being designed and configured for receiving data inputs from the three-dimensional imaging modality, the first position tracking system, the radioactive emission detector and the second position tracking system and calculating the position of the body component and the position of the radiopharmaceutical uptaking portion of the body component in a common system-of-coordinates.

According to yet an additional aspect of the present invention there is provided a method for calculating a position of a body component and a position of a radiopharmaceutical uptaking portion of the body component within a subject, the method comprising the steps of (a) providing a three-dimensional imaging modality being connected to and/or communicating with a first position tracking system and calculating the position of the body component in a first system-of-coordinates; (b) providing a radioactive emission detector being connected to and/or communicating with a second position tracking system and tracking a position of the radiopharmaceutical uptaking portion of the body component in a second system-of-coordinates; and (c) receiving data inputs from the three-dimensional imaging modality, the first position tracking system, the radioactive emission detector and the second position tracking system and calculating the position of the body component and the position of the radiopharmaceutical uptaking portion of the body component in a common system-of-coordinates.

According to still an additional aspect of the present invention there is provided a system for performing an intrabody surgical procedure on a radiopharmaceutical uptaking portion of a body component within a subject, the system comprising (a) a radioactive emission detector being connected to and/or communicating with a first position tracking system for tracking a position of the radiopharmaceutical uptaking portion of the body component in a first system-of-coordinates; (b) a surgical instrument being connected to and/or communicating with a second position tracking system for tracking a position of the surgical instrument in a second system-of-coordinates; and (c) at least one data processor being designed and configured for receiving data inputs from the first position tracking system, the radioactive emission detector and the second position tracking system and for calculating the position of the surgical instrument and the radiopharmaceutical uptaking portion of the body component in a common system-of-coordinates.

According to a further aspect of the present invention there is provided a method for performing an intrabody surgical procedure on a radiopharmaceutical uptaking portion of a body component within a subject, the method comprising the steps of (a) providing a radioactive emission detector being connected to and/or communicating with a first position tracking system and tracking a position of the radiopharmaceutical uptaking portion of the body component in a first system-of-coordinates; (b) providing a surgical instrument being connected to and/or communicating with a second position tracking system and tracking a position of the surgical instrument in a second system-of-coordinates while performing the intrabody surgical procedure; and (c) receiving data inputs from the first position tracking system, the radioactive emission detector and the second position tracking system and calculating the position of the surgical instrument and the radiopharmaceutical uptaking portion of the body component in a common system-of-coordinates while performing the intrabody surgical procedure.

According to further features in preferred embodiments of the invention described below, the second system-of-coordinates serves as the common system-of-coordinates and therefore the position of the radiopharmaceutical uptaking portion of the body component in the first system-of-coordinates is projected onto the second system-of-coordinates.

According to still further features in the described preferred embodiments the first system-of-coordinates serves as the common system-of-coordinates and therefore the position of the surgical instrument in the second system-of-coordinates is projected onto the first system-of-coordinates.

According to still further features in the described preferred embodiments the second system-of-coordinates, the first system-of-coordinates and the common system-of-coordinates are a single system-of-coordinates.

According to still further features in the described preferred embodiments the first system-of-coordinates, the second system-of-coordinates and the common system-of-coordinates are each a separate system-of-coordinates and therefore the position of the surgical instrument in the second system-of-coordinates and the position of the radiopharmaceutical uptaking portion of the body component in the first system-of-coordinates are both projected onto the common system-of-coordinates.

According to still further features in the described preferred embodiments the first position tracking system and the second position tracking system are a single position tracking system.

According to still further features in the described preferred embodiments an image presentation device serves for visual copresentation of the position of the surgical instrument and the radiopharmaceutical uptaking portion of the body component.

According to still further features in the described preferred embodiments the radioactive emission detector is selected from the group consisting of a narrow beam radioactive emission detector and a spatially sensitive radioactivity detector.

According to still further features in the described preferred embodiments the first and the second position tracking systems are each individually selected from the group consisting of an articulated arm position tracking system, an accelerometers based position tracking system, a potentiometers based position tracking system, a sound wave based position tracking system, a radiofrequency based position tracking system and an electromagnetic field based position tracking system.

According to still further features in the described preferred embodiments the surgical instrument is selected from the group consisting of laser probe, cardiac catheter, angioplastic catheter, endoscopic probe, biopsy needle, ultrasonic probe, fiber optic scopes, aspiration tubes, laparoscopy probe, thermal probe and suction/irrigation probe.

According to still further features in the described preferred embodiments the radiopharmaceutical is selected from the group consisting of $^{131}$I, $^{67}$Ga, $^{99}$Tc methoxyisobutyl isonitrile, $^{201}$Tl, $^{18}$F-fluorodeoxyglucose, $^{125}$I-fibrinogen and $^{111}$In-octreotide.

According to still further features in the described preferred embodiments the three-dimensional imaging modality is connected to and/or communicating with a third position tracking system and is used for calculating the position of a body component in a third system-of-coordinates.

According to still further features in the described preferred embodiments data inputs are received from the three-dimensional imaging modality and the third position tracking system and are used for calculating the position of the surgical instrument and the position of the radiopharmaceutical uptaking portion of a body component and the position of the body component in a common system-of-coordinates.

According to still further features in the described preferred embodiments the first position tracking system, the second position tracking system and the third position tracking system are a single position tracking system.

According to still further features in the described preferred embodiments the position of the surgical instrument, the radiopharmaceutical uptaking portion of the body component and the body component are corepresented by a visual presentation device.

According to still further features in the described preferred embodiments each of the first, the second and the third position tracking system is independently selected from the group consisting of an articulated arm position tracking system, an accelerometers based position tracking system, a sound wave based position tracking system, a radiofrequency based position tracking system and an electromagnetic field based position tracking system.

According to still further features in the described preferred embodiments the second system-of-coordinates serves as the common system-of-coordinates and therefore the position of the radiopharmaceutical uptaking portion of the body component in the first system-of-coordinates and the position of the body component in the third system-of-coordinates are projected onto the second system-of-coordinates.

According to still further features in the described preferred embodiments the first system-of-coordinates serves as the common system-of-coordinates and therefore the position of the surgical instrument in the second system-of-coordinates and the position of the body component in the third system-of-coordinates are projected onto the first system-of-coordinates.

According to still further features in the described preferred embodiments the third system-of-coordinates serves as the common system-of-coordinates and therefore the position of the surgical instrument in the second system-of-coordinates and the position of the radiopharmaceutical uptaking portion of the body component in the first system-of-coordinates are projected onto the third system-of-coordinates.

According to still further features in the described preferred embodiments the second system-of-coordinates, the first system-of-coordinates, the third system-of-coordinates and the common system-of-coordinates are a single system-of-coordinates.

According to still further features in the described preferred embodiments the second system-of-coordinates, the first system-of-coordinates, the third system-of-coordinates and the common system-of-coordinates are each a separate system-of-coordinates and therefore the position of the surgical instrument in the second system-of-coordinates and the position of the radiopharmaceutical uptaking portion of the body component in the first system-of-coordinates and the position of the body component in the third system-of-coordinates are all projected onto the common system-of-coordinates.

According to still another aspect of the present invention there is provided a system for generating a two or three dimensional image of a radioactivity emitting source in a body, the system comprising (a) a radioactive emission detector; (b) a position tracking system being connected to and/or communicating with the radioactive emission detector; and (c) a data processor being designed and configured for receiving data inputs from the position tracking system and from the radioactive emission detector and for generating the two or three dimensional image of the radioactivity emitting source.

According to still another aspect of the present invention there is provided a method of generating a two or three dimensional image of a radioactivity emitting source in a body, the system comprising (a) scanning the body with a radioactive emission detector; (b) using a position tracking system being connected to and/or communicating with the radioactive emission detector for determining a position in a three dimensional system of coordinates of the radioactive emission detector; and (c) data processing inputs from the position tracking system and from the radioactive emission detector for generating the two or three dimensional image of the radioactivity emitting source.

The present invention successfully addresses the shortcomings of the presently known configurations by providing a radioactive emission detector connected to or communicating with a position tracking system and the use thereof in a variety of systems and methods used for medical imaging and/or medical procedures.

Implementation of the methods and systems of the present invention involves performing or completing selected tasks or steps manually, automatically, or a combination thereof. Moreover, according to actual instrumentation and equipment of preferred embodiments of the methods and systems of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable algorithms. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
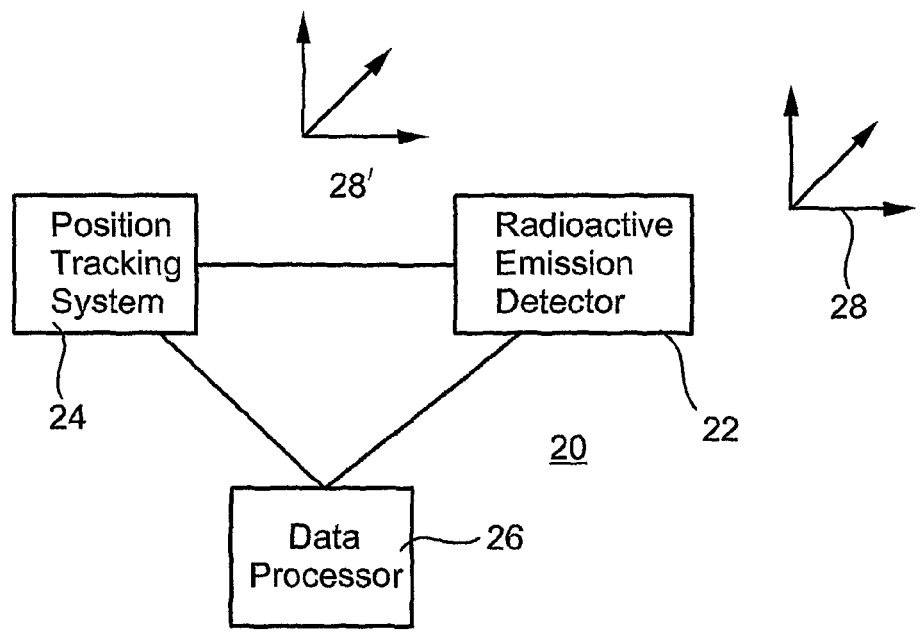
FIG. 1 is a black box diagram of a system according to the teachings of the present invention.

The present invention is of a radioactive emission detector equipped with a position tracking system which can be functionally integrated with medical three-dimensional imaging modalities and/or with guided minimal-invasive or other surgical tools. The present invention can be used for calculating the position of a concentrated radiopharmaceutical in the body in positional context of imaged portions of the body, which information can be used, for example, for performing an efficient and highly accurate minimally invasive surgical procedure.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The use of radioactive materials to tag physiologically active tissue within the body of a patient for determining the tissue's localization and demarcation by radioactive emission detectors has been disclosed in the medical literature for at least forty years. Significant developments in the localization and demarcation of tissue bearing radioactive isotope tags for diagnostic and/or therapeutic purposes have occurred since that time. In fact, it is now becoming an established practice in the diagnosis and/or treatment of certain diseases, e.g., cancer, blood clots and abcesses, to introduce monoclonal antibodies or other agents, e.g., fibrinogen, tagged with a radioactive isotope (e.g., $^{99m}$Technetium, $^{111}$Indium, $^{123}$Iodine, and $^{125}$Iodine) into the body of the patient. Such radiopharmaceuticals tend to localize in particular tissue, whereas uptake or binding of the specific radiopharmaceutical is increased in more "physiologically active" tissue such as the active core of a cancerous tissue, so that the radiation emitted following nuclear disintegrations of the isotope can be detected by a radiation detector to better allocate the active portion of a tumor.

In another type of applications radioactive substances are used to determine the level of flow of blood in blood vessels and the level of perfusion thereof into a tissue, e.g., coronary flow and myocardial perfusion.

Referring now to the drawings, FIG. 1 illustrates a system for calculating a position of a radioactivity emitting source in a system-of-coordinates, in accordance with the teachings of the present invention, which system is referred to hereinbelow as system 20.

System 20 includes a radioactivity emission detector 22. System 20 according to the present invention further includes a position tracking system 24. System 24 is connected to and/or communicating with radioactive emission detector 22 so as to monitor the position of detector 22 in a three-dimensional space defined by a system-of-coordinates 28 in three or more, say four, five or six degrees-of-freedom. System 20 further includes a data processor 26. Data processor 26 is designed and configured for receiving data inputs from position tracking system 24 and from radioactive emission detector 22 and, as is further detailed below, for calculating the position of the radioactivity emitting source in system-of-coordinates 28. The phrases "system-of-coordinates" and "three-dimensional space" are used herein interchangeably.

Position tracking systems per se are well known in the art and may use any one of a plurality of approaches for the determination of position in a three-dimensional space as is defined by a system-of-coordinates in three and up to six degrees-of-freedom. Some position tracking systems employ movable physical connections and appropriate movement monitoring devices to keep track of positional changes. Thus, such systems, once zeroed, keep track of position changes to thereby determine actual positions at all times. One example for such a position tracking system is an articulated arm.

Figure 2:
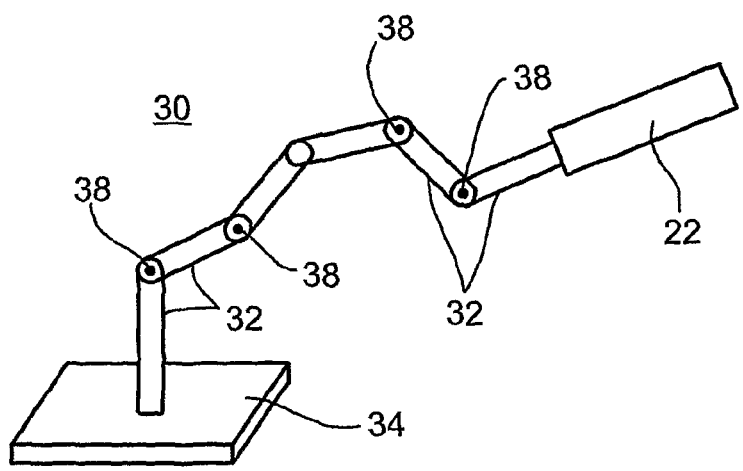
FIG. 2 is a perspective view of an articulated arm which serves as a position tracking system shown carrying a radioactive emission detector in accordance with the teachings of the present invention.

FIG. 2 shows an articulated arm 30 which includes six arm members 32 and a base 34, which can therefore provide positional data in six degrees-of-freedom. Monitoring positional changes may be effected in any one of several different ways. For example, providing each arm member 32 with, e.g., potentiometers 38 used to monitor the angle between adjacent arm members 32 to thereby monitor the angular change of each such aim member with respect to another, so as to determine the position in space of radioactive emission detector 22, which is physically connected to articulated arm 30.

Figure 3:
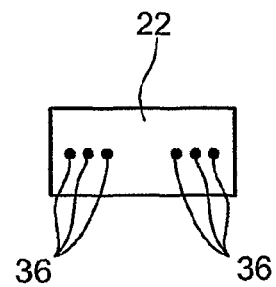
FIG. 3 is a schematic depiction of a radioactive emission detector carrying a pair of three coaxialy aligned accelerometers which serve as a position tracking system in accordance with the teachings of the present invention.

As is shown in FIG. 3 other position tracking systems can be attached directly to radioactive emission detector 22 in order to monitor it's position in space. An example of such a position tracking system is an assortment of three triaxialy (e.g., co-orthogonally) oriented accelerometers 36 which may be used to monitor the positional changes of radioactive emission detector 22 with respect to a space. A pair of such assortments, as is specifically shown in FIG. 3, can be used to determine the position of detector 22 in six-degrees of freedom.

Figure 4:
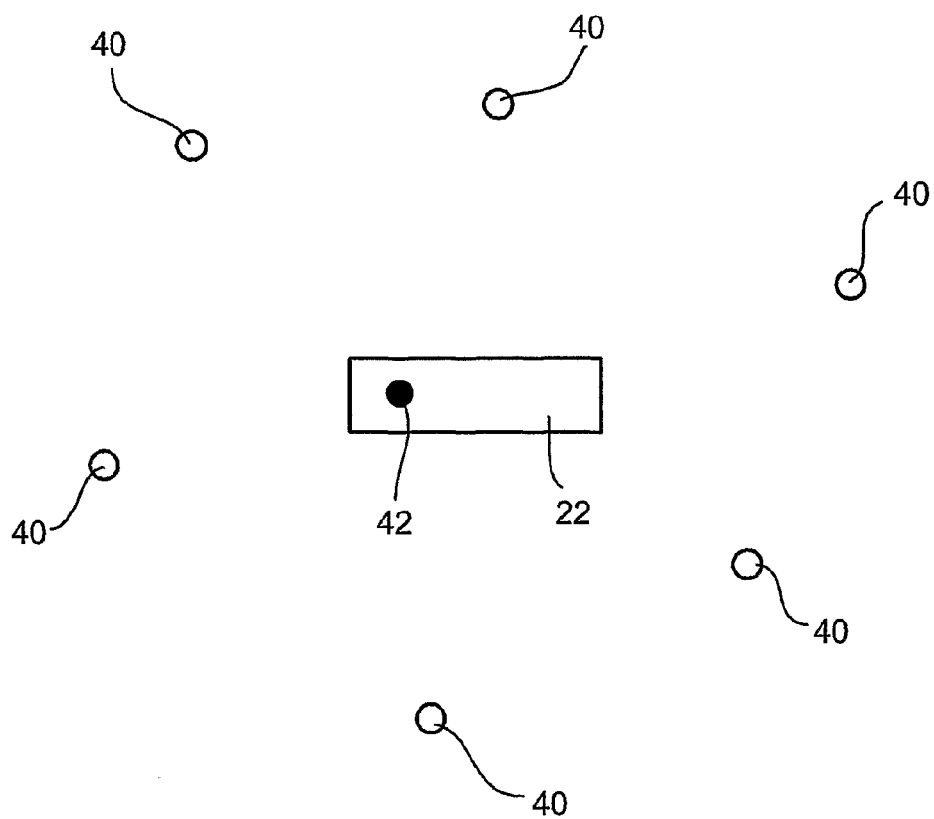
FIG. 4 is a schematic presentation of a radioactive emission detector communicating with yet another type of a position tracking system in accordance with the teachings of the present invention.

As is shown in FIG. 4, other position tracking systems redetermine a position irrespective of previous positions, to keep track of positional changes. Such systems typically employ an array of receivers/transmitters 40 which are spread in known positions in a three-dimensional space and transmitter(s)/receiver(s) 42, respectively, which are in physical connection with the object whose position being monitored. Time based triangulation and/or phase shift triangulation are used in such cases to periodically determine the position of the monitored object, radioactive emission detector 22 in this case. Examples of such a position tracking systems employed in a variety of contexts using acoustic (e.g., ultrasound) or electromagnetic fields are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which are incorporated by reference as if fully set forth herein.

Radioactive emission detectors are well known in the art and may use any one of a number of approaches for the determination of the amount of radioactive emission emanating from an object or portion thereof. Depending on the type of radiation, such detectors typically include substances which when interacting with radioactive decay emitted particles emit either electrons or photons in a level which is proportional over a wide linear range of operation to the level of radiation impinging thereon. The emission of electrons or photons is measurable and therefore serve to quantitatively determine radiation levels.

Figure 5:
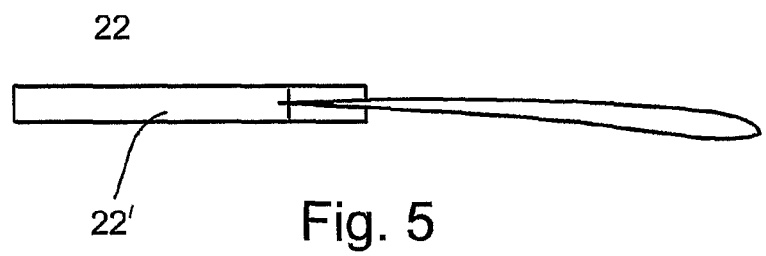
FIG. 5 is a simplified cross-sectional view of a narrow beam radioactive emission detector used to implement an embodiment of the present invention.

As is shown in FIG. 5 one such example is a narrow beam radioactive emission detector 22'. Narrow beam radioactive emission detector 22' includes a narrow slit so as to allow only radiation arriving from a predetermined narrow angular direction to enter the detector.

Figure 6:
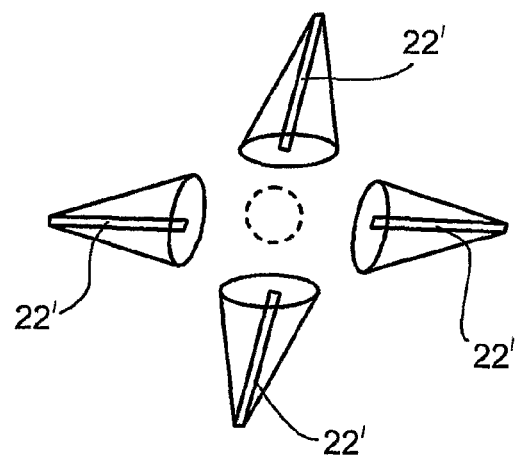
FIG. 6 is a presentation of a scanning protocol which can be effected with the detector of FIG. 5.

As is shown in FIG. 6, such a detector is typically used to measure radioactivity, point by point, by scanning over the surface of a radioactive object from a plurality of directions and distances. In the example shown cone scans from four different directions are employed. It will be appreciated that if sufficient radioactivity records are collected from different angles and distances, and the orientation and position in space of detector 22' is simultaneously monitored and recorded during such scans, a three-dimensional model of a radioactive region can be reconstituted and its position in space determined.

Figure 7:
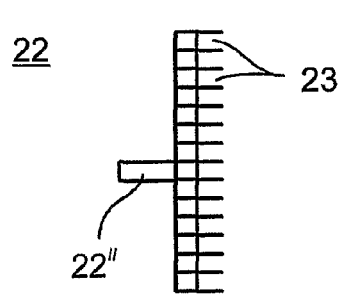
FIG. 7 is a simplified cross-sectional view of a spatially sensitive radioactive emission detector used to implement another embodiment of the present invention.
Figure 8:
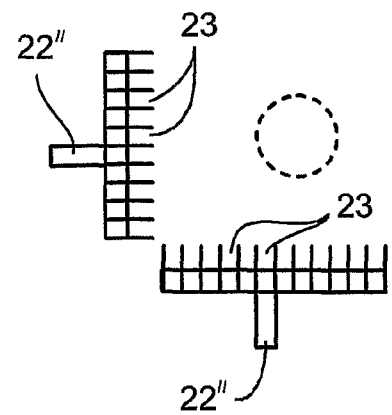
FIG. 8 is a presentation of a scanning protocol which can be effected with the detector of FIG. 7.

FIG. 7 shows another example of a radioactive emission detector, a spatially sensitive radioactive emission detector 22". Detector 22", in effect, includes an array of multitude narrow beam detector units 23. Such an arrangement is used in accordance with the teachings of the present invention to reduce the amount of measurements and angles necessary to acquire sufficient data so as to reconstitute a three-dimensional model of the radioactive object. Examples of spatially sensitive radioactive emission detectors employed in a variety of contexts are disclosed in, for example, U.S. Pat. Nos. 4,019,057; 4,550,250; 4,831,262; and 5,521,373; which are incorporated by reference as if fully set forth herein. An additional example is the COMPTON detector (http://www.ucl.ac.uk/MedPhys/posters/giulia/giulia.htm). FIG. 8 shows a scan optionally made by spatially sensitive radioactive emission detector 22".

Thus, as now afforded by the present invention, connecting a radioactive emission detector to a position tracking system, permits simultaneous radioactivity detecting and position tracking at the same time. This enables the accurate calculation of the shape, size and contour of the radiating object and it's precise position in a three-dimensional space.

The present invention thus provides a method for defining a position of a radioactivity emitting source in a system-of-coordinates. The method is effected by (a) providing a radioactive emission detector which is connected to or communicating with a position tracking system; and (b) monitoring radioactivity emitted from the radioactivity emitting source, while at the same time, monitoring the position of radioactive emission detector in the system-of-coordinates, thereby defining the position of the radioactivity emitting source in the system-of-coordinates.

It will be appreciated by one of skills in the art that the model produced by system 20 is projectable onto any number of other systems-of coordinates, or alternatively, the system-of-coordinates defined by position tracking system 24 may be shared by other position tracking systems, as is further detailed hereinunder, such that no such projection is required.

Thus, as is further shown in FIG. 1, system 20 of the present invention can be used for calculating a position of a radioactivity emitting source in a first system-of-coordinates 28 and further for projecting the position of the radioactivity emitting source onto a second system-of-coordinates 28'. The system includes radioactive emission detector 22, position tracking system 24 which is connected to and/or communicating with radioactive emission detector 22, and data processor 26 which is esigned and configured for (i) receiving data inputs from position tracking system and from radioactive emission detector; (ii) calculating the position of the radioactivity emitting source in the first system-of-coordinates; and (iii) projecting the position of the radioactivity emitting source onto the second system-of-coordinates.

A method for calculating a position of a radioactivity emitting source in a first system-of-coordinates and for projecting the position of the radioactivity emitting source onto a second system-of-coordinates is also offered by the present invention. This method is effected by (a) providing a radioactive emission detector being connected to or communicating with a position tracking system; and (b) monitoring radioactivity being emitted from the radioactivity emitting source, while at the same time, monitoring the position of the radioactive emission detector in the first system-of-coordinates, thereby defining the position of the radioactivity emitting source in the first system-of-coordinates and projecting the position of the radioactivity emitting source onto the second system-of-coordinates.

It will be appreciated that the combination of a radioactive emission detector and a position tracking system connected thereto and/or communicating therewith a suitable data processor can be used for generating a two or three dimensional image of the radioactivity emitting source. An algorithm can be used to calculate image intensity based on, for example, a probability function which averages radiation counts and generates an image in which the shorter the time interval between radioactive counts, the brighter the image and vise versa, while compensating when a location is re-scanned. A free hand scanning with a directional detector can be employed for this purpose.

In one embodiment, when scanning a body area with the detector, the detector is made to follow a three dimensional surface which defines the body curvatures and in effect is used also as a position tracking pointer. This information can be used to define the position of the radioactive source with respect to the outer surface of the body, so as to create a three dimensional map of both the radioactive source and the body. This approach can also be undertaken in open surgeries, such as open chest surgeries so as to provide the surgeon in real time with information concerning the functionality of a tissue.

The radioactive emission detector which can be used in context of the present invention can be either a beta emission detector, a gamma emission detector, or a combination of both beta and gamma emission detector. The latter detector can be used to improve localization by sensing for example gamma emission distant from the source and sensing beta or positrons emission closer to the source. A beta detector is dedicated for the detection of either electrons from sources such as $^{131}$Iodine, or positrons from sources such as $^{18}$Fluor. A gamma detector can be designed as a single energy detector or as a detector that can distinguish between different types of energies, this can be achieved, for example, by using scintillation crystals of different width. The latter configuration is useful to closely locate a radiation source such as a beta or positron source, since low energy gamma radiation generated by the COMPTON effect, or stopping radiation effect will be more confined to the vicinity of the radiation source. Also, the detector can be designed to utilize coincidence detection by using detectors facing one another (180 degrees) with the examined organ or tissue in-between. The radiation detector can have different collimators, such as a collimator with multiple slits for high sensitivity lower spatial resolution. When approaching the radiation source it can be switched to a single slit higher resolution, lower sensitivity collimator. A shutter can be placed in front of the detector, so as to achieve a similar effect.

System 20 of the present invention can be used in synergetic concert with other medical devices, such as, but not limited to, any one of a variety of imaging modalities and/or surgical instruments.

Imaging modalities are well known in the art, the main modalities that serve for three-dimensional imaging are a fluoroscope, a computerized tomography scanner, a magnetic resonance imager and an ultrasound imager and an optical camera.

Medical images taken of the human body are typically acquired or displayed in three main orientations (i) coronal orientation: in a cross section (plane), for example, across the shoulders, dividing the body into front and back halves; (ii) sagittal orientation: in a cross section (plane), for example, down the middle, dividing the body into left and right halves; and (iii) axial orientation: in a cross section (plane), perpendicular to the long axis of the body, dividing the body into upper and lower halves. Oblique views can also be acquired and displayed.

Various types of X-Ray imaging are central to diagnosis of many types of cancer. Conventional x-ray imaging has evolved over the past 100 years, but the basic principal is still the same as in 1895. An x-ray source is turned on and x-rays are radiated through the body part of interest and onto a film cassette positioned under or behind the body part. The energy and wavelength of the x-rays allows them to pass through the body part and create the image of the internal structures like bones of the hand. As the x-rays pass through the hand, for instance, they are attenuated by the different density tissues they encounter. Bone attenuates a great deal more of the x-rays than the soft tissue around it because of its grater density. It is these differences in absorption and the corresponding varying exposure level of the film that creates the images.

Fluoroscopy is a method based on the principals of film x-ray that is useful for detecting disorders and tumors in the upper gastro-intestinal (GI) system (for example, the stomach and intestines). Fluoroscopic imaging yields a moving x-ray picture. The doctor can watch the screen and see a dynamic image of the patient's body (for example the beating heart). Fluoroscopic technology improved greatly with the addition of television cameras and fluoroscopic "image intensifiers". Today, many conventional X-ray systems have the ability to switch back and forth between the radiographic and fluoroscopic modes. The latest x-ray systems have the ability to acquire the radiograph or fluoroscopic movie using digital acquisition.

Computed Tomography (CT) is based on the x-ray principal, where the film is replaced by a detector that measures the x-ray profile. Inside the covers of the CT scanner is a rotating frame which has an x-ray tube mounted on one side and the detector mounted on the opposite side. A fan beam of x-ray is created as the rotating frame spins the x-ray tube and detector around the patient. Each time the x-ray tube and detector make a 360° rotation, an image or "slice" has been acquired. This "slice" is collimated to a thickness between 1 mm and 10 mm using lead shutters in front of the x-ray tube and x-ray detector.

As the x-ray tube and detector make this 360° rotation, the detector takes numerous profiles of the attenuated x-ray beam. Typically, in one 360° lap, about 1,000 profiles are sampled. Each profile is subdivided spatially by the detectors and fed into about 700 individual channels. Each profile is then backwards reconstructed (or "back projected") by a dedicated computer into a two-dimensional image of the "slice" that was scanned.

The CT gantry and table have multiple microprocessors that control the rotation of the gantry, movement of the table (up/down and in/out), tilting of the gantry for angled images, and other functions such as turning the x-ray beam on an off. The CT contains a slip ring that allows electric power to be transferred from a stationary power source onto the continuously rotating gantry. The innovation of the power slip ring has created a renaissance in CT called spiral or helical scanning. These spiral CT scanners can now image entire anatomic regions like the lungs in a quick 20 to 30 second breath hold. Instead of acquiring a stack of individual slices which may be misaligned due to slight patient motion or breathing (and lung/abdomen motion) in between each slice acquisition, spiral CT acquires a volume of data with the patient anatomy all in one position. This volume data set can then be computer-reconstructed to provide three-dimensional pictures such as of complex blood vessels like the renal arteries or aorta. Spiral CT allows the acquisition of CT data that is perfectly suited to three-dimensional reconstruction.

MR Imaging is superior to CT in detecting soft tissue lesions such as tumors as it has excellent contrast resolution, meaning it can show subtle soft-tissue changes with exceptional clarity. Thus, MR is often the method of choice for diagnosing tumors and for searching for metastases. MR uses magnetic energy and radio waves to create cross-sectional images or "slices" of the human body. The main component of most MR systems is a large tube shaped or cylindrical magnet. Also, there are MR systems with a C-shaped magnet or other type of open design. The strength of the MR systems magnetic field is measured in metric units called "Tesla". Most of the cylindrical magnets have a strength between 0.5 and 1.5 Tesla and most of the open or C-shaped magnets have a magnetic strength between 0.01 and 0.35 Tesla.

Inside the MR system a magnetic field is created. Each total MR examination typically is comprised of a series of 2 to 6 sequences. An "MR sequence" is an acquisition of data that yields a specific image orientation and a specific type of image appearance or "contrast". During the examination, a radio signal is turned on and off, and subsequently the energy which is absorbed by different atoms in the body is echoed or reflected back out of the body. These echoes are continuously measured by "gradient coils" that are switched on and off to measure the MR signal reflecting back. In the rotating frame of reference, the net magnetization vector rotate from a longitudinal position a distance proportional to the time length of the radio frequency pulse. After a certain length of time, the net magnetization vector rotates 90 degrees and lies in the transverse or x-y plane. It is in this position that the net magnetization can be detected on MRI. The angle that the net magnetization vector rotates is commonly called the 'flip' or 'tip' angle. At angles greater than or less than 90 degrees there will still be a small component of the magnetization that will be in the x-y plane, and therefore be detected. Radio frequency coils are the "antenna" of the MRI system that broadcasts the RF signal to the patient and/or receives the return signal. RF coils can be receive-only, in which case the body coil is used as a transmitter; or transmit and receive (transceiver). Surface coils are the simplest design of coil. They are simply a loop of wire, either circular or rectangular, that is placed over the region of interest.

A digital computer reconstructs these echoes into images of the body. A benefit of MRI is that it can easily acquire direct views of the body in almost any orientation, while CT scanners typically acquire images perpendicular to the long body axis.

Ultrasound imaging is a versatile scanning technique that uses sound waves to create images of organs or anatomical structures in order to make a diagnosis. The ultrasound process involves placing a small device called a transducer, against the skin of the patient near the region of interest, for example, against the back to image the kidneys. The ultrasound transducer combines functions of emitting and receiving sound. This transducer produces a stream of inaudible, high frequency sound waves which penetrate into the body and echo off the organs inside. The transducer detects sound waves as they echo back from the internal structures and contours of the organs. Different tissues reflect these sound waves differently, causing a signature which can be measured and transformed into an image. These waves are received by the ultrasound machine and turned into live pictures with the use of computers and reconstruction software.

Ultrasound scanning has many uses, including: diagnosis of disease and structural abnormalities, helping to conduct other diagnostic procedures, such as needle biopsies etc.

There are limitations to some ultrasound techniques: good images may not be obtained in every case, and the scan may not produce as precise results as some other diagnostic imaging procedures. In addition, scan results may be affected by physical abnormalities, chronic disease, excessive movement, or incorrect transducer placement.

In many cases imaging modalities either inherently include (e.g., fluoroscope, CT, MRI) and/or are integrated with position-tracking-systems, which enable the use of such systems to reconstruct three-dimensional image models and provide their position in a three-dimensional space.

It will be appreciated that, similar to the vision system, also an optical camera can be used to generate three-dimensional imagery date according to the present invention by imaging a body from a plurality (at least two) directions. This type of imaging is especially applicable in open chest surgeries or other open surgeries. Software for calculating a three dimensional image from a pair of stereoscopic images is well known in the art.

Thus, as used herein and in the claims section that follows, the phrase "three-dimensional imaging modality" refers to any type of imaging equipment which includes software and hardware for generating a three dimensional image. Such an equipment can generate a three dimensional image by imaging successive cross-sections of a body, e.g., as if viewed from a single direction. Alternatively, such an equipment can generate a three dimensional image by imaging a body from different angles or directions (typically two angles) and thereafter combining the data into a three dimensional image.

Surgical instruments are also well known in the art and may use any one of a plurality of configurations in order to perform minimal-invasive surgical procedures. Examples include laser probes, cardiac and angioplastic catheters, endoscopic probes, biopsy needles, aspiration tubes or needles, ultrasonic probes, fiber optic scopes, laparoscopy probes, thermal probes and suction/irrigation probes. Examples of such surgical instruments employed in a variety of contexts are disclosed in, for example, U.S. Pat. Nos. 6,083,170; 6,063,022; 5,954,665; 5,840,025; 5,718,241; 5,713,946; 5,694,945; 5,568,809; 5,546,951; 5,480,422 5,391,199, 5,800,414; 5,843,017; 6,086,554; 5,766,234; 5,868,739; 5,911,719; 5,993,408; 6,007,497; 6,021,341; 6,066,151; 6,071,281; 6,083,166 and 5,746,738, which are incorporated by reference as if fully set forth herein.

For some applications, examples of which are provided in the list of patents above, surgical instruments are integrated with position-tracking-systems, which enable to monitor the position of such instruments while placed in and guided through the body of a treated patient.

In some minimally-invasive procedures even the position of the patient him or herself is monitored via a position tracking system, using, for example, electronic feducial markers attached at certain locations to the patient's body.

Thus, as is further detailed hereinunder, by projecting the three-dimensional data and positions received from any of the above mentioned devices into a common system of coordinates, or alternatively, employing a common position tracking system for all of these devices, one can integrate the data into a far superior and comprehensive presentation.

Figure 9:
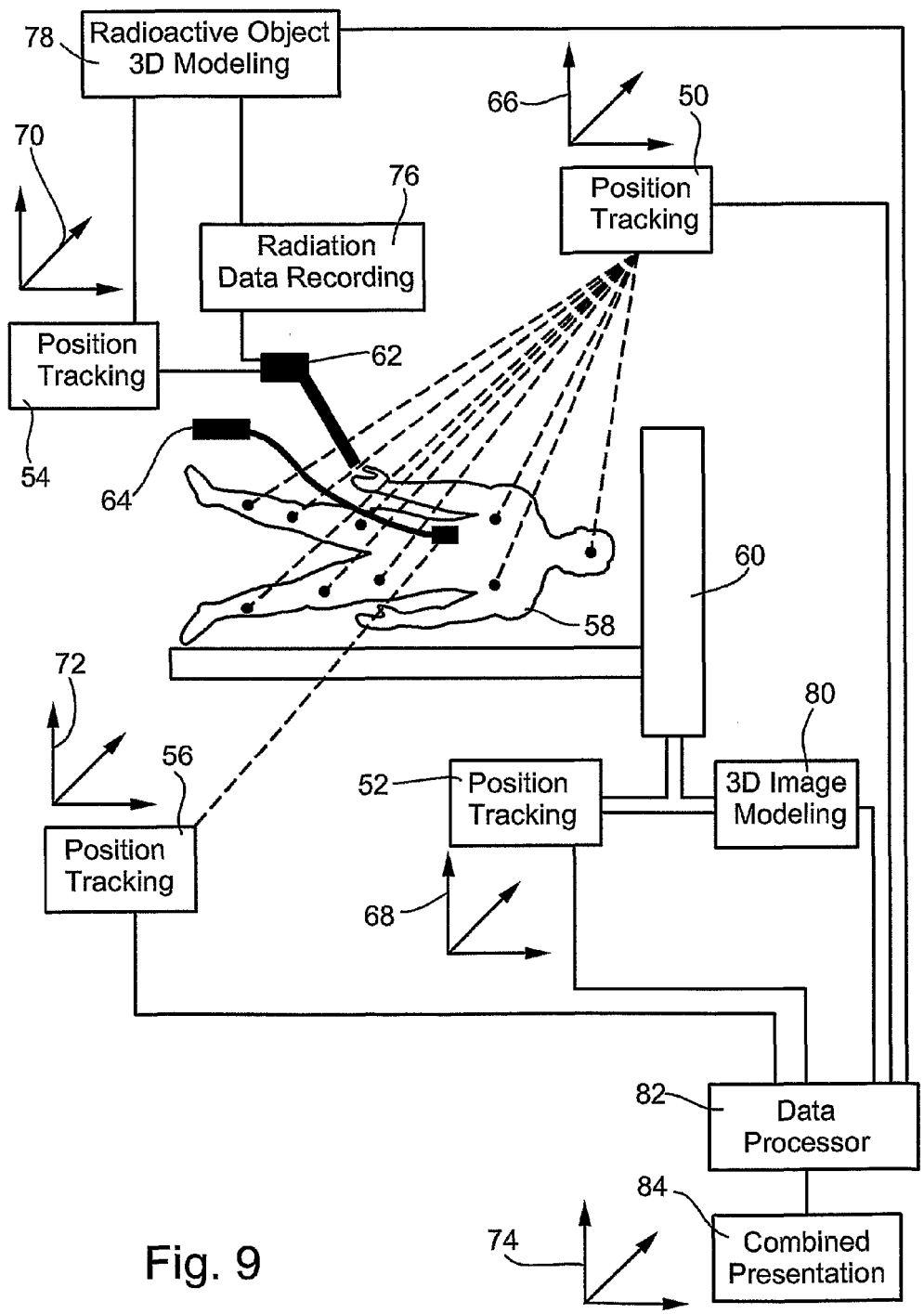
FIG. 9 demonstrates a system in accordance with the teachings of the present invention which employs four position tracking systems for co-tracking the positions of a patient, a radioactive emission detector, an imaging modality and a surgical instrument.

An example to this effect is shown in FIG. 9. In the embodiment shown, four independent position tracking systems 50, 52, 54 and 56 are used to track the positions of a patient 58, an imaging modality 60, a radioactive emission detector 62 and a surgical instrument 64 in four independent systems-of-coordinates 66, 68, 70 and 72, respectively. If the patient is steel, no tracking of the patient's position is required.

It will be appreciated that any subset or all of the position tracking systems employed may be integrated into one or more common position tracking systems, and/or that any subset or all of the position tracking systems employed may share one or more systems-of-coordinates, and further that any positional data obtained by any of the position tracking systems described in any of the systems-of coordinates may be projected to any other system of coordinates or to an independent (fifth) system of coordinates 74. In one preferred embodiment, applicable for applications at the torso of the patient, the system of coordinates is a dynamic system of coordinates which takes into account the chest breathing movements of the patient during the procedure.

As indicated at 76, the radioactive data collected by detector 62 is recorded and, as indicated at 78, the position and the radioactive data records are used to generate a three-dimensional model of a radiopharmaceutical uptaking portion of a body component of the patient.

Similarly, as indicated at 80, the imagery data collected by imaging modality 60 is recorded and the position and the imagery data records are used to generate a three-dimensional model of the imaged body component of the patient.

All the data collected is then fed into a data processor 82 which processes the data and, as indicated at 84, generates a combined or superimposed presentation of the radioactive data and the imagery data, which is in positional context with patient 58 and surgical instrument 64.

Instrument 64, which by itself can be presented in context of the combined presentation, may then be used to perform the procedure most accurately. Processor 82 may be a single entity or may include a plurality of data processing stations which directly communicate with, or even integral to, any one or more of the devices described.

The present invention provides a major advantage over prior art designs because it positionally integrates data pertaining to a body portion as retrieved by two independent imaging techniques, conventional imaging and radioactive imaging, to thereby provide a surgeon with the ability the fine point the portion of the body to be sampled or treated.

It will be appreciated that subsets of the devices described in FIG. 9 may be used as stand-alone systems. For example, a combination of detector 62 with its position-tracking system and instrument 64 with its position-tracking-system may in some instances be sufficient to perform intrabody procedures. For mere diagnostic purposes a combination of detector 62 position-tracking-system and modality 60 position-tracking-system are sufficient.

The following provides a list of known procedures which can take advantage of the system and method of the present invention:

In cancer diagnosis the system and method of the present invention can find uses for screening for cancer and/or directing invasive diagnosis (biopsies) either from outside the body or by way of endoscopic approach. Examples include, but are not limited to, lung cancer biopsy, breast cancer biopsy, prostate cancer biopsy, cervical cancer biopsy, liver cancer biopsy, lymph node cancer biopsy, thyroid cancer biopsy, brain cancer biopsy, bone cancer biopsy, colon cancer biopsy, gastro intestine cancer endoscopy and biopsy, endoscopic screening for vaginal cancer, endoscopic screening for prostate cancer (by way of the rectum), endoscopic screening for ovarian cancer. (by way of the vagina), endoscopic screening for cervical cancer (by way of the vagina), endoscopic screening for bladder cancer (by way of the urinary track), endoscopic screening for bile cancer (by way of the gastrointestinal track), screening for lung cancer, screening for breast cancer, screening for melanoma, screening for brain cancer, screening for lymph cancer, screening for kidney cancer, screening for gastro intestinal cancer (from the outside).

Procedures known as directing localized treatment of cancer can also benefit from the system and method of the present invention. Examples include, but are not limited to, intra tumoral chemotherapy, intra tumoral brachytherapy, intra tumoral cryogenic ablation, intra tumoral radio frequency ablation, intra tumoral ultrasound ablation, and intra tumoral laser ablation, in cases of, for example, lung cancer, breast cancer, prostate cancer, cervical cancer, liver cancer, lymph cancer, thyroid cancer, brain cancer, bone cancer, colon cancer (by way of endoscopy through the rectum), gastric cancer (by way of endoscopy through the thorax), thoracic cancer, small intestine cancer (by way of endoscopy through the rectum or, by way of endoscopy through the thorax), bladder cancer, kidney cancer, vaginal cancer and ovarian cancer.

In interventional cardiology the following procedures can take advantage of the present invention wherein the method and system can be used to assess tissue perfusion, tissue viability and blood flow intra operatively during PTCA procedure (balloon alone or in conjunction with the placement of a stent), in cases of cardiogenic shock to assess damage to the heart, following myocardial infarct to assess damage to the heart, in assessing heart failure condition tissue in terms of tissue viability and tissue perfusion, in intra vascular tissue viability and perfusion assessment prior to CABG operation.

Using the method and system of the present invention to assess tissue perfusion, tissue viability and blood flow intra operatively can also be employed in the following: during CABG operation to assess tissue viability, to mark infarct areas, during CABG operations to assess the success of the re vascularization.

It will be appreciated that many other procedures may also take advantage of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for obtaining a distribution of a radioactivity emitting source in a system-of-coordinates, the device comprising:
   (a) a radioactive emission detector for imaging a three-dimensional space comprising the radioactivity emitting source;
   (b) a positioning instrument configured for carrying said radioactive emission detector to perform a plurality of radioactivity measurements of a radioactivity emitting source from a plurality of locations and directions;
   (c) a position tracking device which monitors a position of said radioactive emission detector in relation to said three-dimensional space; and
   (d) a data processor which reconstructs a three dimensional (3D) image of the radioactivity emitting source from a plurality of said radioactivity measurements with a varying spatial resolution and obtains a positional distribution of said radioactive emitting source using measurements of a same area from multiple locations having different resolution according to said position.

2. The device of claim 1, wherein said position tracking device is selected from the group consisting of an articulated arm position tracking device, an accelerometers based position tracking device, a potentiometers based position tracking device, a sound wave based position tracking device, a radio frequency based position tracking device, an electromagnetic field based position tracking device, and an optically based position tracking device.

3. The device of claim 1, wherein said radioactive emission detector is configured for free-hand scanning, and whose position is monitored by said position tracking device in a first system-of-coordinates, further comprising:
   a surgical instrument whose position is monitored by an additional position tracking device for tracking a position of said surgical instrument in a second system-of-coordinates and at least one data processor being designed and configured for receiving data inputs from said position tracking device, said radioactive emission detector and said additional position tracking device and for calculating the position of the surgical instrument and the radiopharmaceutical uptaking portion of the body component in a common system-of-coordinates.

4. The device of claim 3, wherein said first position tracking device and said second position tracking device are a single position tracking device.

5. The device of claim 3, further comprising an image presentation device which serves for visual co-presentation of the position of said surgical instrument and the radiopharmaceutical uptaking portion of the body component.

6. The device of claim 3, wherein said surgical instrument is selected from the group consisting of laser probe, cardiac catheter, angioplastic catheter, endoscopic probe, biopsy needle, ultrasonic probe, fiber optic scopes, aspiration tubes, laparoscopy probe, thermal probe and suction/irrigation probe.

7. The device of claim 1, wherein said position is a positional change.

8. The device of claim 1, wherein said detector performs said plurality of radioactivity measurements in different resolutions.

9. The device of claim 1, wherein said data processor reconstructs said image according to radioactivity measurements having different resolutions.

10. The device of claim 1, wherein said detector performs said plurality of radioactivity measurements from different angles and distances.

11. The device of claim 1, wherein said spatial resolution is higher for radioactivity measurements as the detector approaches the radiation source.

12. A method for reconstructing a radiopharmaceutical uptaking portion of a body component within a subject, the method comprising:
   (a) providing radioactive emission detector supported by a positioning instrument;
   (b) using said radioactive emission detector for performing a plurality of radioactivity measurements of a radiopharmaceutical uptaking portion from a plurality of locations and directions;
   (c) receiving data inputs from said radioactive emission detector; and
   (d) reconstructing according to said data inputs a three dimensional (3D) model of said radiopharmaceutical uptaking portion;
      wherein said performing comprises monitoring a position of said radioactive emission detector in relation to said radiopharmaceutical uptaking portion and calculating a spatial 3D resolution of said three dimensional model, and
      wherein said three dimensional model is reconstructed using measurements of a same area from multiple locations having different spatial resolution according to said locations.

13. The method for claim 12, wherein said radioactive emission detector communicates with an image presentation device which serves for visual presentation of said radiopharmaceutical uptaking portion.

14. The method of claim 12, and further including monitoring changes of the radiopharmaceutical uptaking portion of the body component as a function of time, responsive to treatment.

15. The method of claim 12, and further including monitoring changes of the radiopharmaceutical uptaking portion of the body component as a function of time, responsive to treatment, selected from the group consisting of chemotherapy, brachytherapy, cryogenic ablation, radio frequency ablation, ultrasound ablation, and laser ablation.

16. The method of claim 12, wherein said performing comprises:
   (a) monitoring a position of said radioactive emission detector using a first position tracking device, thus obtaining a position of the radiopharmaceutical uptaking portion of the body component in a first system-of-coordinates;
   (b) monitoring a position of a surgical instrument using a second position tracking device, thus tracking a position of said surgical instrument in a second system-of-coordinates while performing an intrabody surgical procedure; and
   (c) receiving data inputs from said first position tracking device, said radioactive emission detector and said second position tracking device and calculating the position of the surgical instrument and the radiopharmaceutical uptaking portion of the body component in a common system-of-coordinates while performing the intrabody surgical procedure.

17. The method of claim 16, further comprising co-presenting the position of said surgical instrument and the radiopharmaceutical uptaking portion of the body component.

18. The method of claim 12, wherein said monitoring a position of said radioactive emission detector comprises moving said radioactive emission detector in six degrees of freedom.

19. The method of claim 12, wherein said monitoring a position of said radioactive emission detector comprises continuously moving said radioactive emission detector during said performing.

20. The method of claim 12, wherein said monitoring a position of said radioactive emission detector comprises switching between a plurality of collimators to allow performing said plurality of radioactivity measurements at said plurality of spatial resolutions from a common location.

21. The method of claim 12, further comprising tracking positional changes of said positioning instrument in relation to said radioactivity emitting source, said performing is carried out with respect to said tracking.

22. A method for scanning a radioactivity emitting source in a three dimensional space comprising a radioactivity emitting source, comprising:

using a positioning instrument for carrying a radioactive emission detector to perform a scan from a plurality of directions at multiple sites around said three dimensional space while changing a position of said radioactive emission detector in at least three degrees of freedom to image the radioactivity emitting source;

monitoring a positional change of said radioactive emission detector in relation to the three dimensional space during said scan;

computing a spatial 3D resolution change according to said positional change, using measurements with a varying spatial resolution of a same area from multiple locations at different sensitivities; and generating a three dimensional (3D) image of said three dimensional space according to said spatial 3D resolution change.

23. The method of claim 22, wherein said using comprises using an articulated arm for carrying said radioactive emission detector.

24. The method of claim 22, wherein said using comprises using a gantry for carrying said radioactive emission detector instrument.

25. The method of claim 22, wherein said scanning is performed from anterior, inferior, and lateral positions around the three dimensional space.

26. The method of claim 22, wherein said changing comprises changing said position in at least four degrees.

27. The method of claim 22, wherein said changing comprises changing said position in at least five degrees.

* * * * *